United States Patent
Doyle

(10) Patent No.: US 9,357,983 B2
(45) Date of Patent: Jun. 7, 2016

(54) METHOD OF MAKING REDUCED BACKLASH JOINT

(75) Inventor: Mark Doyle, Del Mar, CA (US)

(73) Assignee: CAREFUSION 2200, INC., San Diego, CA (US)

(*) Notice: Subject to any disclaimer, the term of this patent is extended or adjusted under 35 U.S.C. 154(b) by 497 days.

(21) Appl. No.: 13/702,525

(22) PCT Filed: Jun. 7, 2011

(86) PCT No.: PCT/US2011/039402
§ 371 (c)(1),
(2), (4) Date: Mar. 18, 2013

(87) PCT Pub. No.: WO2011/156340
PCT Pub. Date: Dec. 15, 2011

(65) Prior Publication Data
US 2013/0172858 A1  Jul. 4, 2013

Related U.S. Application Data

(60) Provisional application No. 61/354,042, filed on Jun. 11, 2010.

(51) Int. Cl.
*F16G 13/00* (2006.01)
*A61B 17/00* (2006.01)
(Continued)

(52) U.S. Cl.
CPC ............ *A61B 17/00* (2013.01); *B21L 11/00* (2013.01); *F16D 3/42* (2013.01); *F16G 13/02* (2013.01); *F16G 13/08* (2013.01); *F16G 13/10* (2013.01); *A61B 2017/00314* (2013.01); *A61B 2017/00526* (2013.01); *A61B 2017/3409* (2013.01); *B23P 2700/11* (2013.01); *F16D 2250/00* (2013.01); *Y10T 29/49826* (2015.01); *Y10T 29/49865* (2015.01); *Y10T 29/49936* (2015.01)

(58) Field of Classification Search
CPC ............... Y10T 29/49936; Y10T 29/49865; Y10T 29/49876; B23P 2700/11; F16G 13/08; F16G 13/02
USPC .......................................................... 29/521
See application file for complete search history.

(56) References Cited

U.S. PATENT DOCUMENTS

| | | | | |
|---|---|---|---|---|
| 4,349,954 A | * | 9/1982 | Banks | B23K 17/00 29/458 |
| 2006/0213752 A1 | * | 9/2006 | Murakami | B65G 17/086 198/643 |
| 2008/0086857 A1 | * | 4/2008 | Stevenson | B21D 39/037 29/17.2 |

(Continued)

FOREIGN PATENT DOCUMENTS

| | | | | |
|---|---|---|---|---|
| JP | 54001382 A | * | 1/1979 | B29C 65/08 |
| JP | 0297552 A2 | * | 1/1989 | B21D 39/03 |

*Primary Examiner* — Jermie Cozart
(74) *Attorney, Agent, or Firm* — Arent Fox LLP

(57) ABSTRACT

A joint and a corresponding method of creating a precision-fit joint, including creating a mating surface on a first joint component so that the mating surface includes one or more interfering features, connecting a second joint component with the mating surface such that the interfering feature is compressed, and heating the mating surface above a glass transition temperature or melting temperature of the mating surface, or otherwise treating the surface, so as to induce flow of material from the interfering feature to a area of relatively low pressure between the first joint component and the second joint component.

7 Claims, 29 Drawing Sheets

(51) Int. Cl.
*F16G 13/08* (2006.01)
*F16D 3/42* (2006.01)
*F16G 13/10* (2006.01)
*B21L 11/00* (2006.01)
*F16G 13/02* (2006.01)
*A61B 17/34* (2006.01)

(56) References Cited

U.S. PATENT DOCUMENTS

2008/0231042 A1\* 9/2008 Brayman ............... B23P 11/025
 285/41

\* cited by examiner

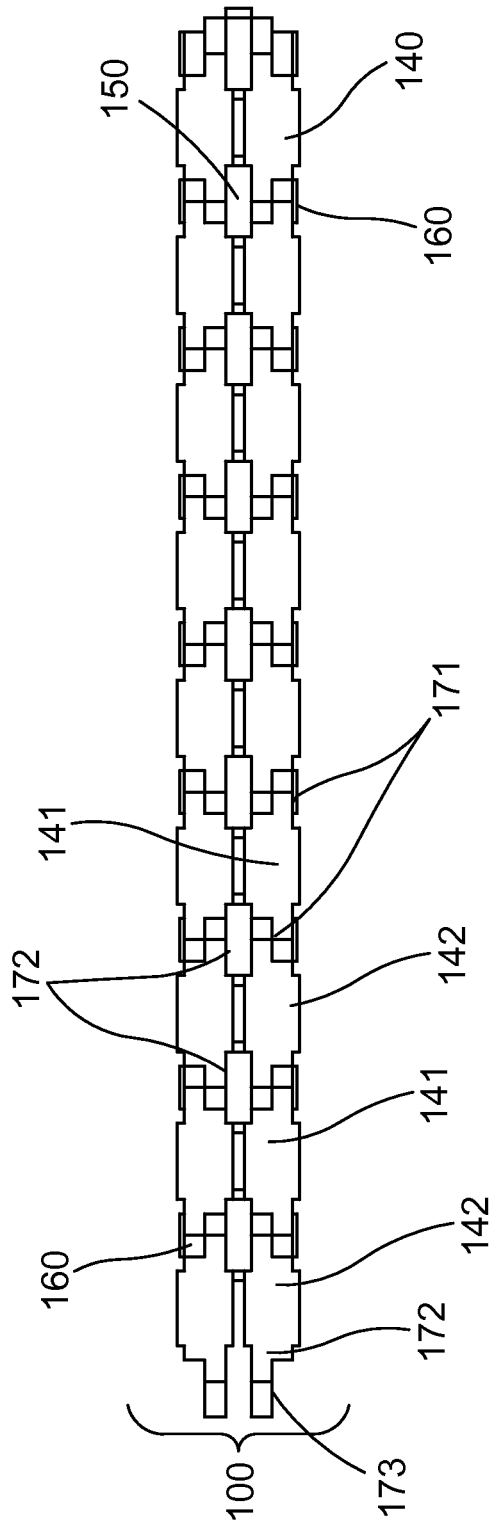
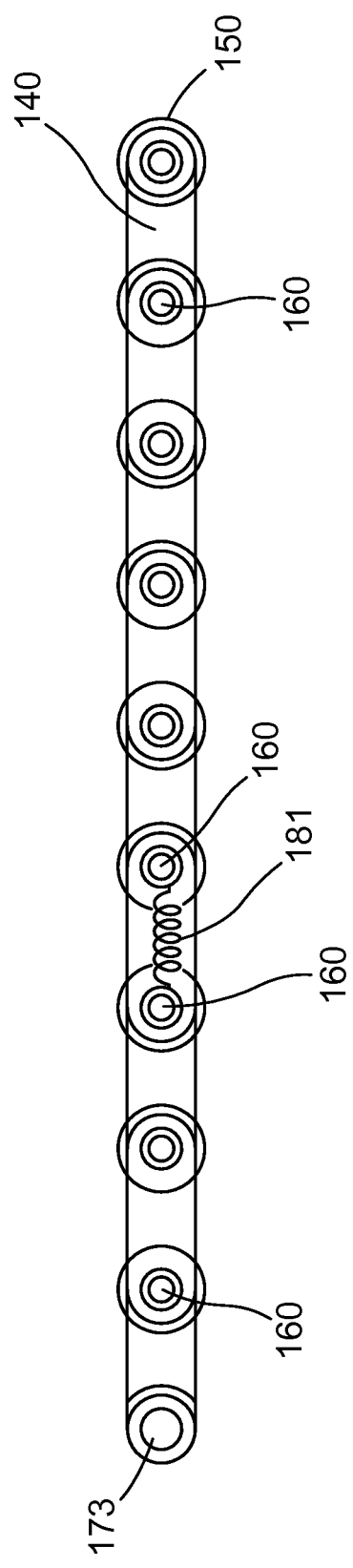
FIG. 3A
FIG. 3B

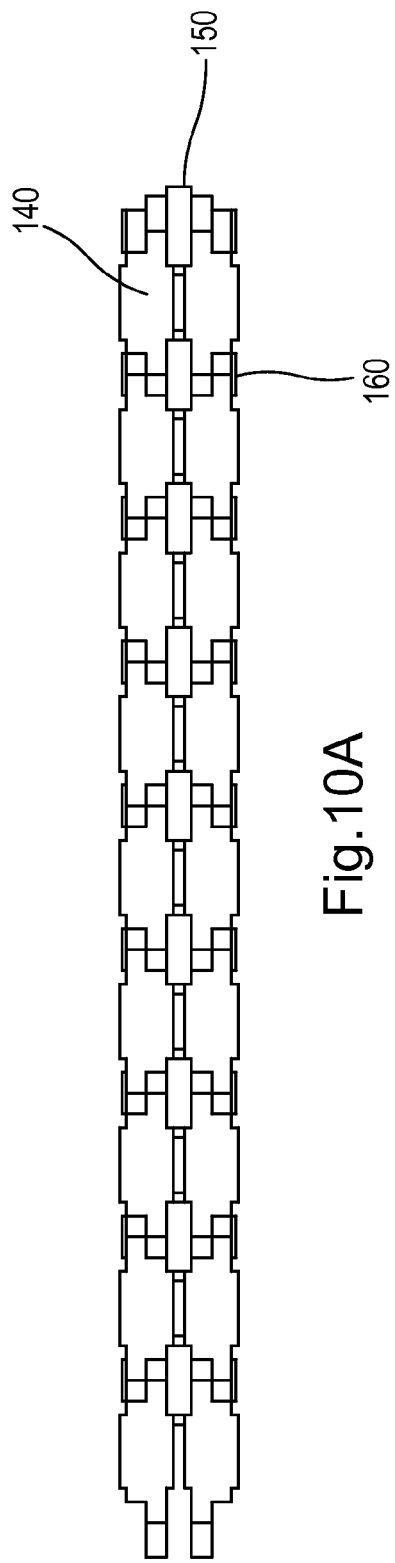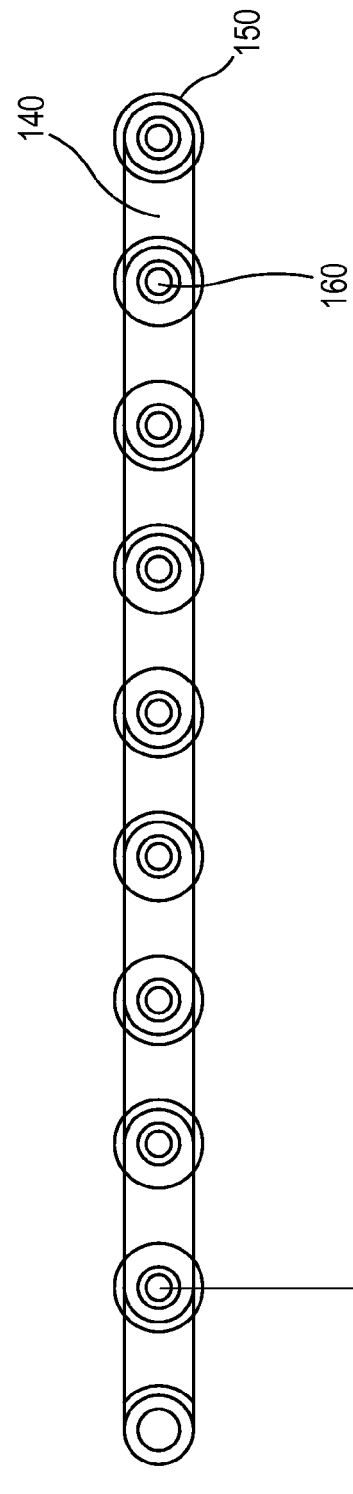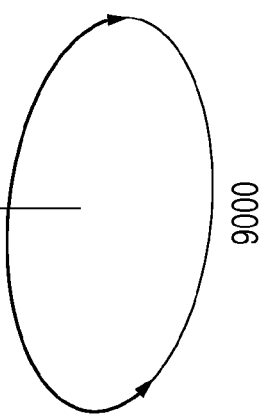

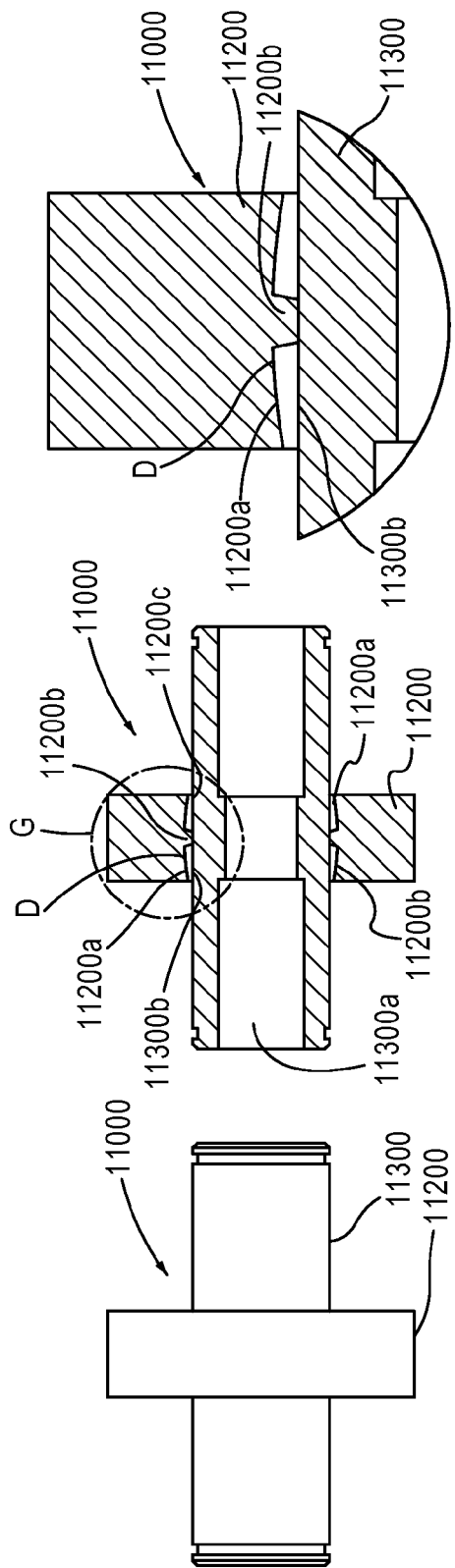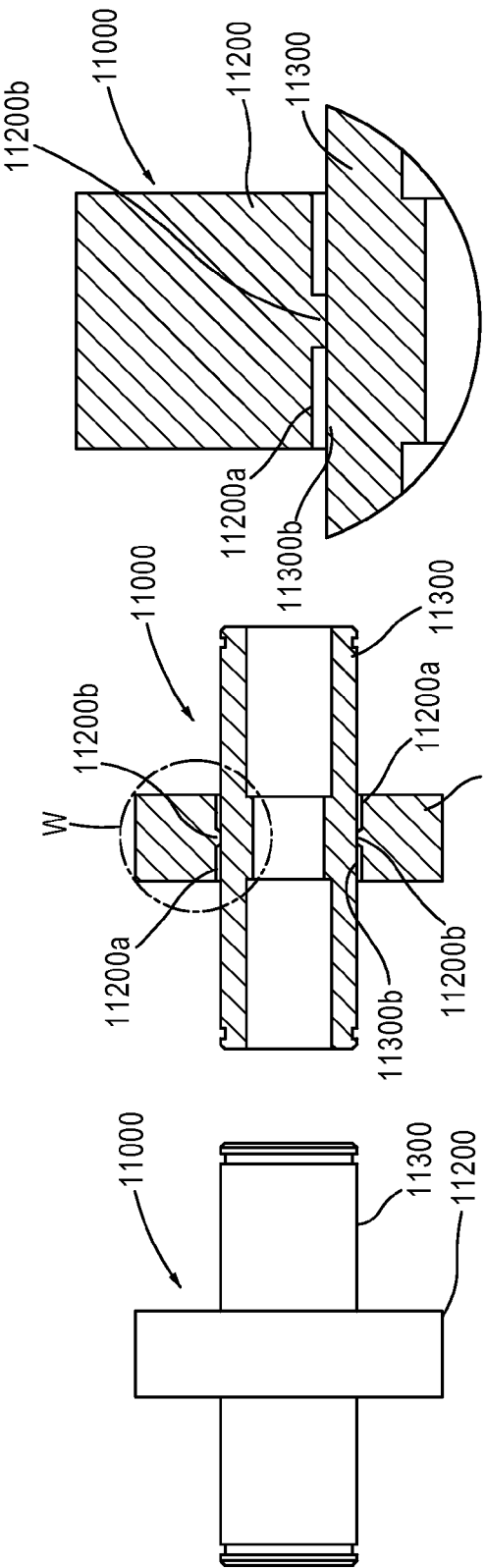

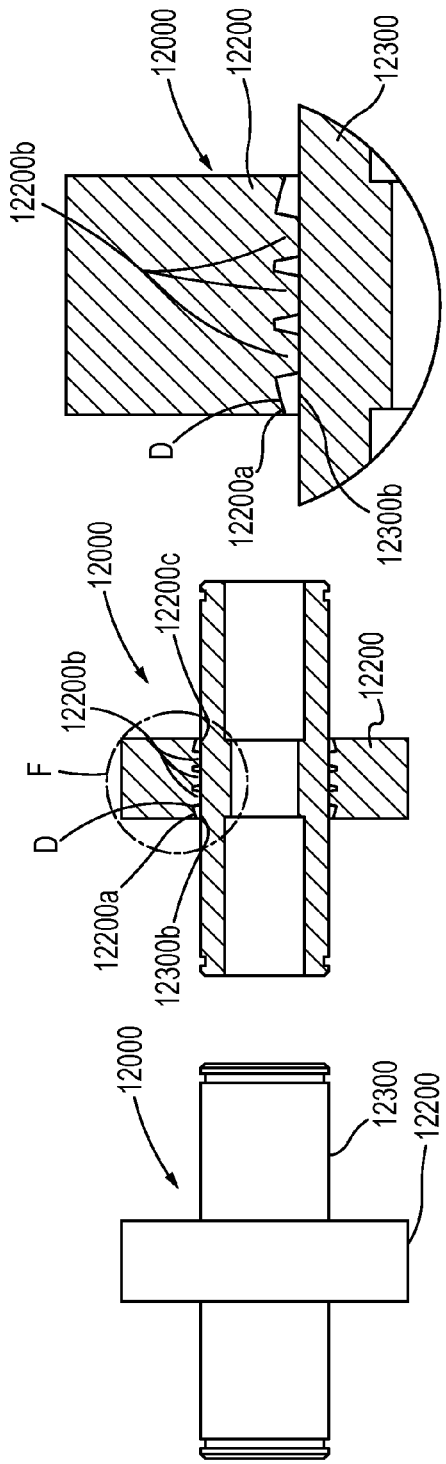

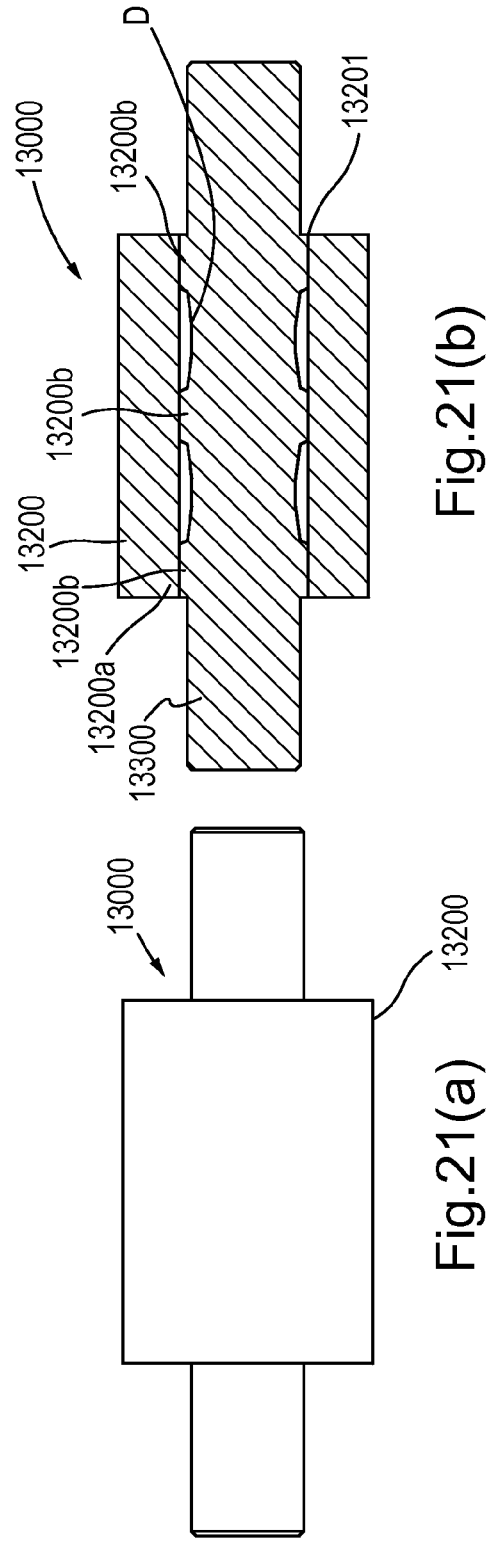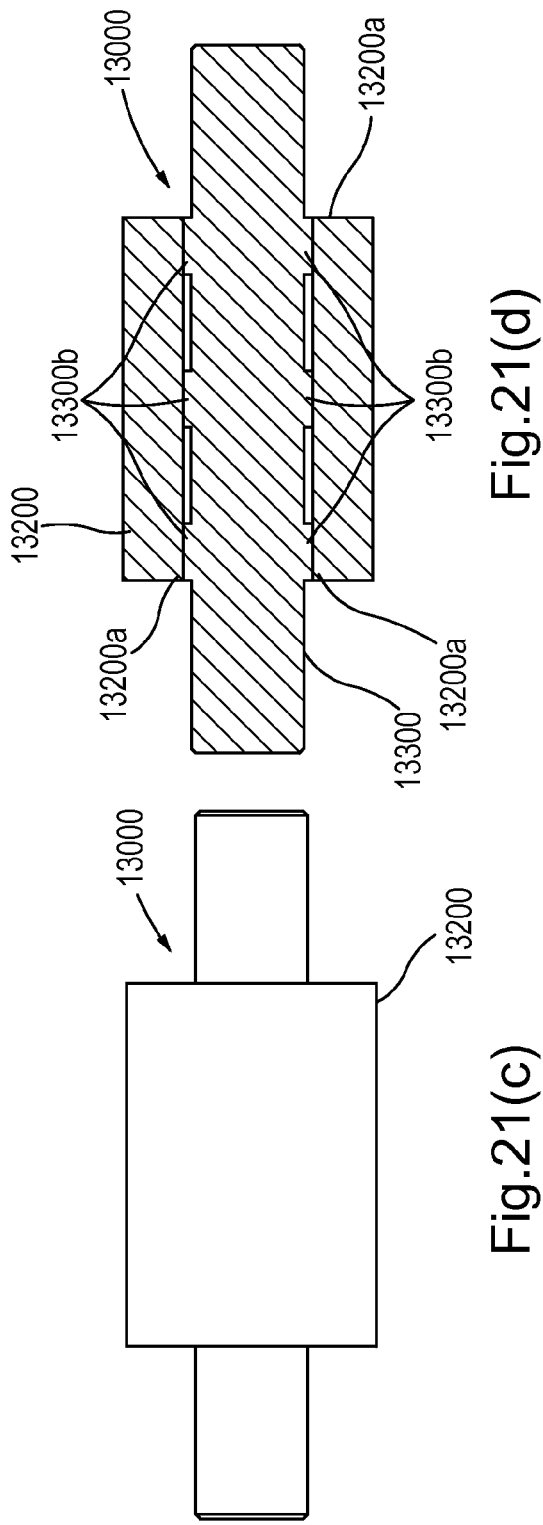

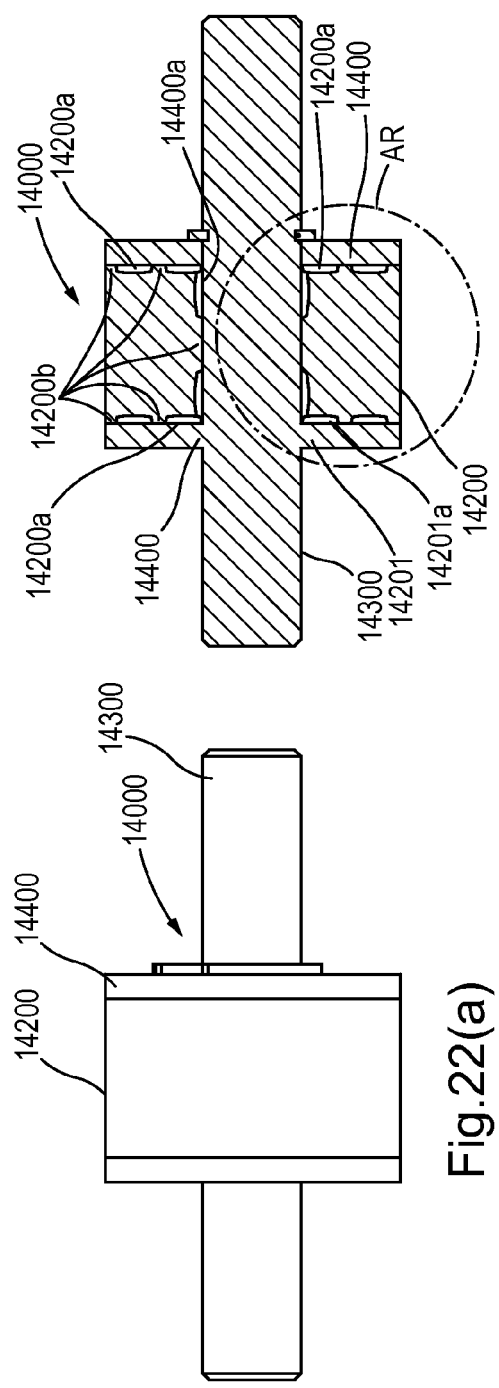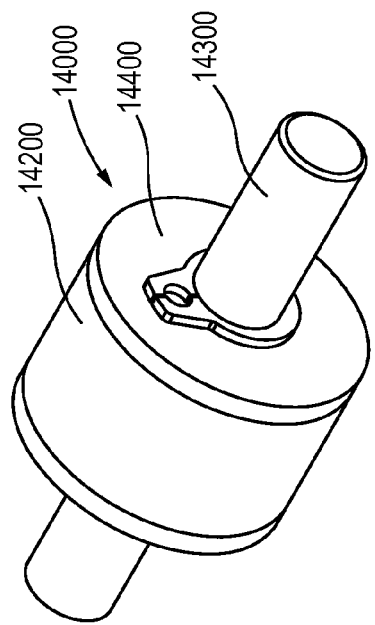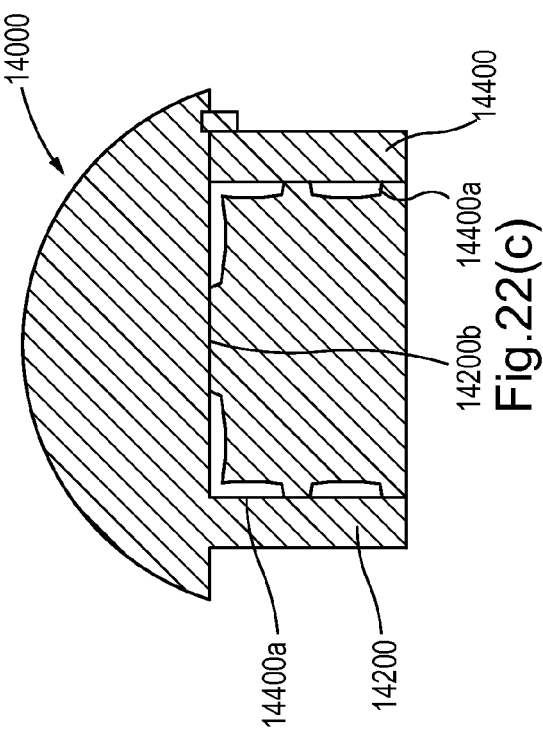

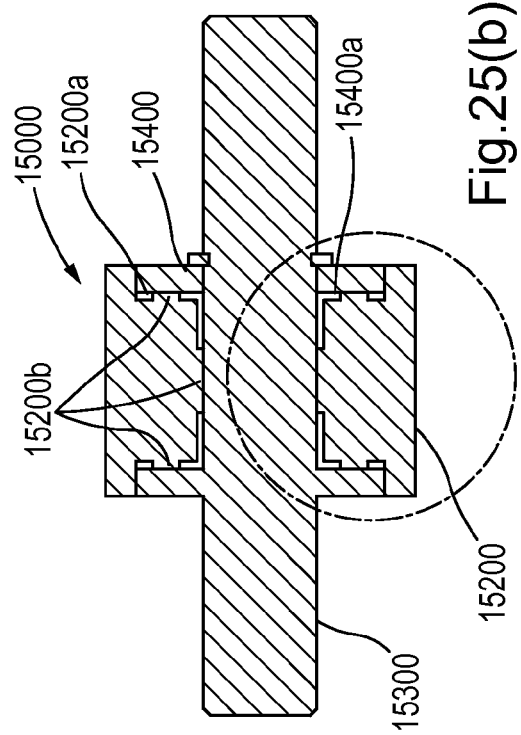
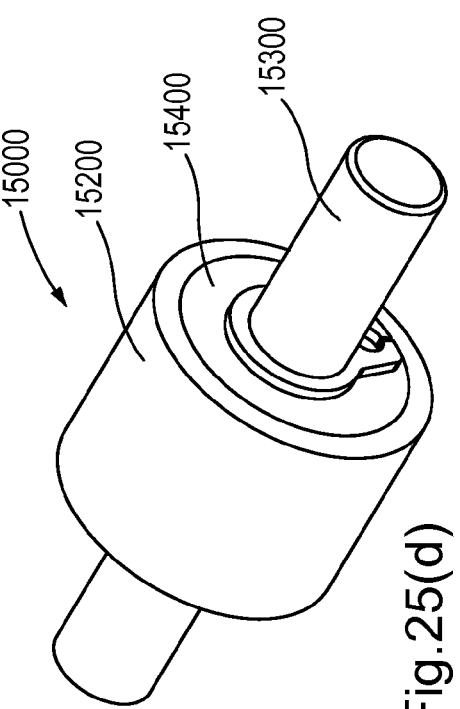
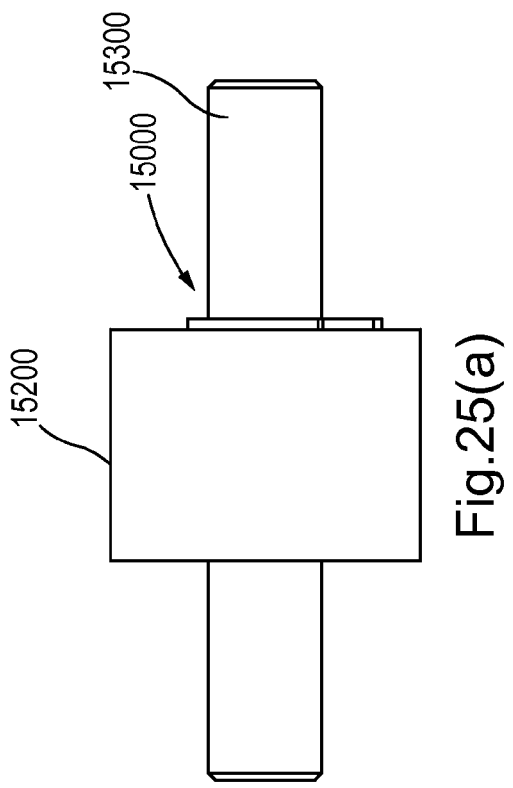
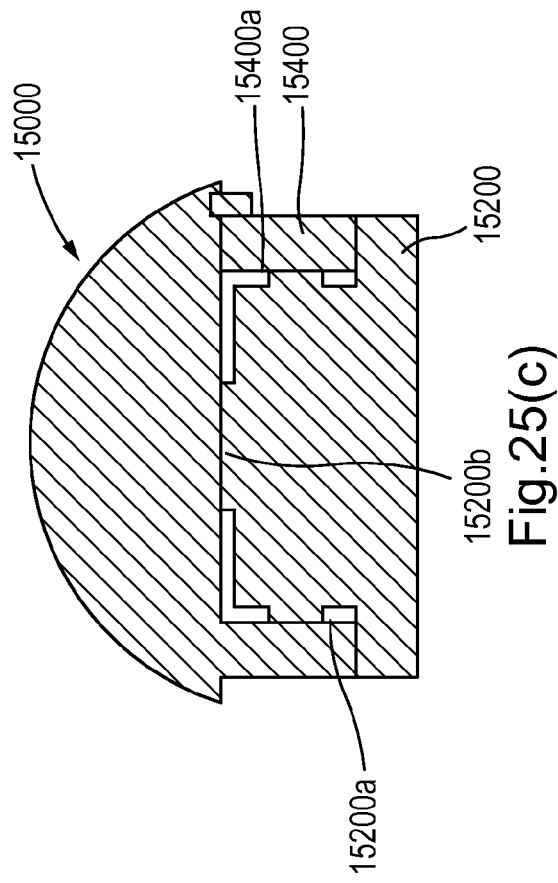

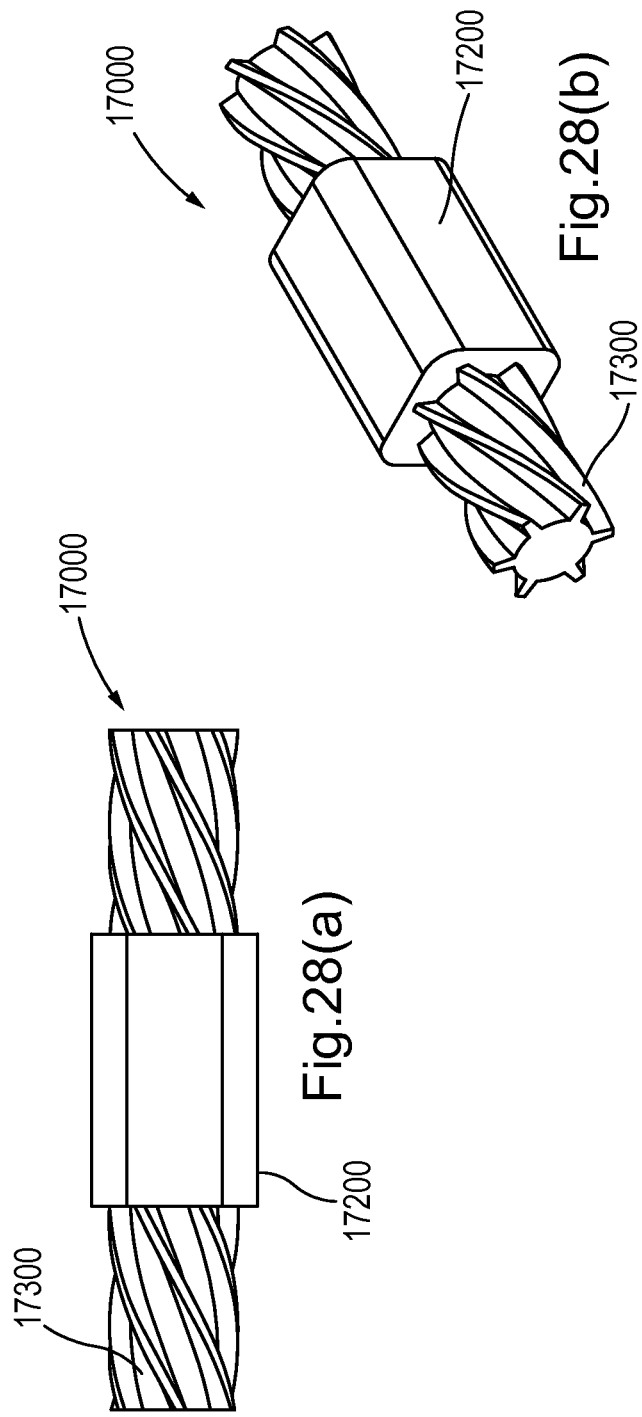

METHOD OF MAKING REDUCED BACKLASH JOINT

CROSS-REFERENCE TO RELATED APPLICATIONS

This application is a National Stage entry of International Application No. PCT/US2011/039402, filed Jun. 7, 2011, which claims priority to U.S. Provisional Appl. No. 61/354,042 filed on Jun. 11, 2010. This application is also related to Applicant's co-pending PCT Appl. No. PCT/US1OI46,619 titled "ARTICULATED SURGICAL TOOL" filed on Aug. 25, 2010, co-pending PCT Appl. No. PCTIUS2OI 1/022562 titled "OVERFORCE MECHANISM" filed Jan. 26, 2011, and is related to co-pending PCT Appl. No. PCT/US2OII/022086 titled "HYDRAULIC DEVICE INCLUDING A SPOOL VALVE" filed Jan. 21, 2011, the entirety of each of which is hereby incorporated by reference herein.

BACKGROUND

1. Field of the Invention

Aspects of the present invention relate to a reduced backlash joint, and a method of making same.

2. Background of the Related Art

Mechanisms for transmitting mechanical force, particularly those transmitting force around corners and bends, often employ joints, fittings or matings. One example such joint in the related art is that used in drive chains for remote actuation of components. In this example, such joints and chains are needed in surgical environments to permit work to be performed in difficult-to-reach areas, such as may occur during abdominal surgery. It is of general interest to ensure that such joints or fittings fit as closely as possible for certain applications.

One problem that can occur with such drive chains when certain fit is not close is called "backlash." Backlash between connecting joint components, for example links in a chain, can occur when the joint or chain is pushed or pulled for mechanical actuation, or generally when a mechanical component is actuated, for example in rotary or linear motion, or in the case of a universal joint in complex multi-axis motion.

In particular, fitting issues or "give" between joint components or links/connection components such as might be used, for example, in an actuating chain, can cause such backlash when the joint components or links/connection components are used to transmit force. For example, in a surgical use, backlash in the push or pull of a joint components or links/connection components in an actuating chain that controls end effectors or tools in a remotely actuated surgical device during surgery may cause imprecise movements, resulting in over- or under-compensation or other imprecise activating motions on the part of the user. Such over- or under-compensation, or other imprecise activating motion, may lead to accidents or sloppiness in a remotely-actuated surgical procedure. Moreover, "give" in the joint or chain makes its motion less intuitive for the user and, therefore, less easily and precisely controlled, making precision work more difficult.

Although precision machining of components of such chains can, in some cases, improve precision actuation, such machining is often expensive and difficult. It can be especially difficult to machine, with precision, mating surfaces on chain links that are often responsible for the "give" or backlash effect described above.

Therefore, improvements in joint components or links/connection components and general mechanisms are desired.

SUMMARY

The described aspects herein relate to the creation of precision fits between mechanical components by thermal modification of a lower melting point component in an interference relation to a higher melting point, or non-melting, component. The described aspects relate to providing relief features into which displaced material from the lower melting point component can flow.

Additional aspects of the present invention relate to reducing backlash in joints, such as joints used in couplings or chains for transmitting force or motion. While the discussion of the aspects of the present invention that follows uses a remote surgical actuator for an illustrative purpose, it should be appreciated that the environment to which aspects of the present invention may be applied is not limited to surgery and may be used in a variety of other environments. In particular, variations of the invention described herein can be used in any suitable actuating device or application. For example, aspects of the present invention may be used in manufacturing, construction, assembly lines, handling and disposing of hazardous materials, underwater manipulations, handling high temperature materials, or any other suitable environment where a user may be remote from the item being manipulated or may experience fatigue when operating a mechanical device.

With regard to one aspect of the present invention, although many different types of coupling or chain materials may be used, the coupling or chain may include ceramic, metal or other roller features embedded in polymeric links that, themselves, are held together by metal pins. Fitting issues may occur between the mating surfaces of links with other portions, including the metal pins. In these aspects, a precisely fitted joint may be achieved through heating, or applying another treatment to, at least one component, in order to cause a form fit due to a deformation relative to the other component in the joint or chain. For example, in one aspect, induction heating is used to create a precise fit without the extra cost and difficulty of precision machining. In this, or other processes, intentional interference fit may be relieved by melting lower temperature material through heating a higher temperature material forced against it.

In one aspect of the present invention, a method of creating a precision-fit joint, includes: creating a mating surface on a first joint component so that the mating surface includes one or more interfering features; connecting a second joint component with the mating surface, such that the interfering feature is compressed; and heating the mating surface above a glass transition temperature or melting temperature of the mating surface, so as to induce flow of material from the interfering feature to a non-compressed area between the first joint component and the second joint component. In another aspect, the above configuration is reversed, e.g., such that the interfering feature is a non-flowing component. This aspect may include, for example, a shaft with ribs that melt into a mating surface of another component.

In another aspect of the present invention, a method to create a precision-fit chain for an actuating device includes: creating a mating surface on a chain link so that the mating surface includes one or more interfering features; bringing a pin in contact with the mating surface on the chain link, such that the interfering feature of the mating surface is compressed against the pin; and heating the pin to induce heating of the mating surface of the chain link above a glass transition temperature or melting temperature of the chain link, so as to induce flow of material from the interfering feature to an area of relatively low pressure between the chain link and the pin.

Aspects of the present invention provide benefits and advantages that include the ability to create a precision fitting joint, such as in a drive chain for remote actuation, while limiting the need for expensive, precision machining. Aspects of the present invention also provide benefits and advantages that include preventing or diminishing unwanted vibration and imprecision in couplings used for remote actuation, while limiting the need for expensive, precision machining. Thus, a joint, coupling or drive chain for remote actuation can be made more robust and precise at lower cost.

Additional advantages and novel features relating to aspects of the present invention will be set forth in part in the description that follows, and in part will become more apparent to those skilled in the art upon examination of the following or upon learning by practice of aspects thereof.

BRIEF DESCRIPTION OF THE DRAWINGS

Aspects of the present invention will become fully understood from the detailed description given herein below and the accompanying drawings, which are given by way of illustration and example only, and thus not limited with respect to aspects thereof, wherein:

FIG. 1B contains a perspective view of an example system in which aspects of the present invention could be utilized in a track in an actuating device;

FIG. 3A is a view of an example chain prior to induction heating or other treatment, for use in accordance with aspects of the present invention;

FIG. 3B is a side view of the chain of FIG. 3A;

FIG. 10A is a view of an example chain after induction heating or other treatment, in accordance with aspects of the present invention;

FIG. 10B is another view of the induction heating or other treatment of FIG. 10A;

FIGS. 19(a) to 19(f) contain partial cutaway views of another example system that may be implemented in accordance with aspects of the present invention;

FIGS. 20(a) to 20(f) are partial, cutaway, and other views of another example system that may be used in accordance with aspects of the present invention;

FIGS. 21(a) to 21(d) show various views of another example of system portions in accordance with aspects of the present invention;

FIGS. 22(a) to 23(d) show various views of another example of system portions in accordance with aspects of the present invention;

FIGS. 24(a) to 25(d) show various views of another example of system portions in accordance with aspects of the present invention;

FIGS. 28(a) to 28(c) show various views of another example of system portions in accordance with aspects of the present invention.

DETAILED DESCRIPTION

Aspects of the present invention will now be described more fully hereinafter with reference to the accompanying drawings, in which variations and aspects of the present invention are shown. Aspects of the present invention may, however, be realized in many different forms and should not be construed as limited to the variations set forth herein; rather, the variations are provided so that this disclosure will be thorough and complete in the illustrative implementations, and will fully convey the scope thereof to those skilled in the art.

Unless otherwise defined, all technical and scientific terms used herein have the same meaning as commonly understood by one of ordinary skill in the art to which aspects of the present invention belong. The methods and examples provided herein are illustrative only and not intended to be limiting.

Figure 1A:
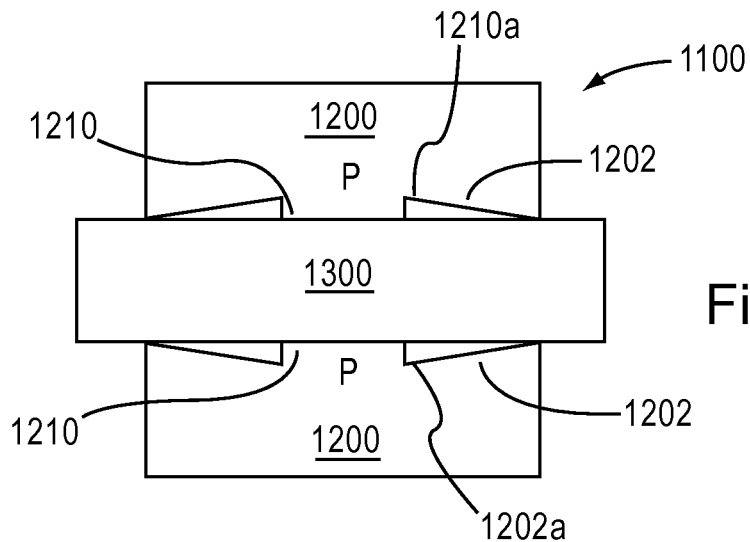
FIGS. 1(a) to 1(c) contain overview portions of a representative joint or component in a process of precision-fitting, in accordance with aspects of the present invention.
Figure 1B:
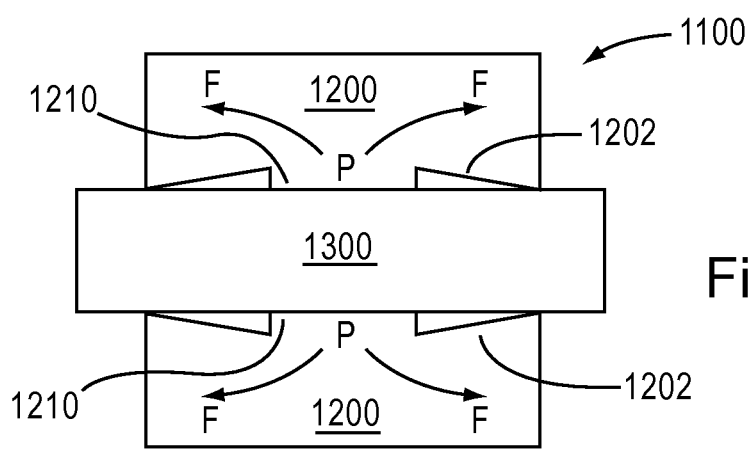
Figure 1C:
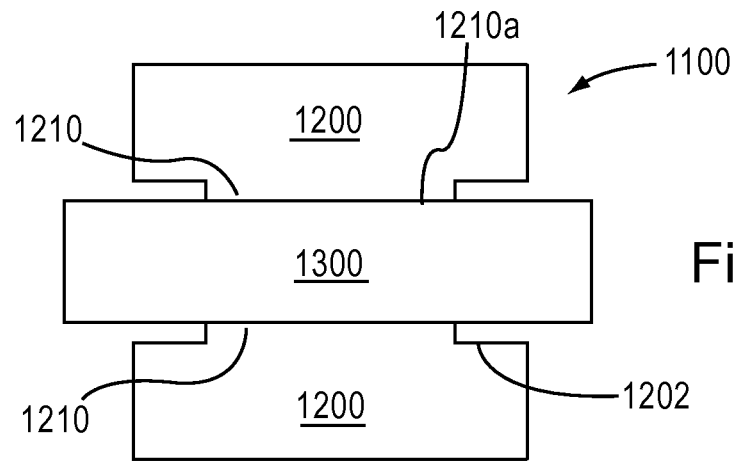
Figure 1B:
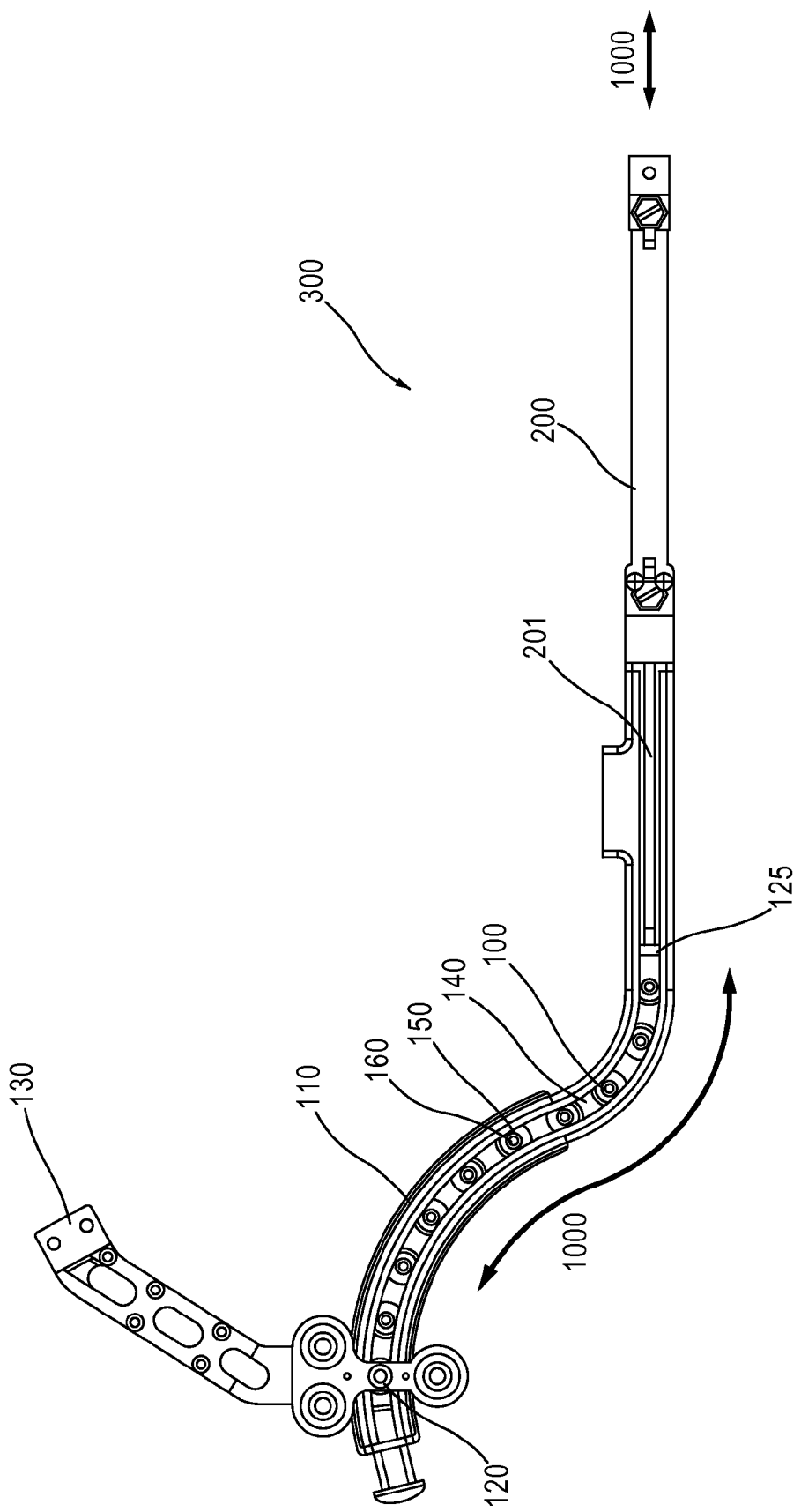

FIG. 1(a) is an overview of a process of precision-fitting a joint or component, in accordance with aspects of the present invention. FIG. 1(a)-1(c) show cut out views of a joint system 1100, including a joint component 1200 and a mating component 1300 in various stages of the precision fit. In the first stage, shown in FIG. 1(a), the mating component 1300 is brought into contact with a surface 1202 of the joint component 1200, as shown. The surface 1202 includes at least one interfering feature 1210. The interfering feature 1210 is fashioned so that when the mating component 1300 is in contact with the surface 1202, and more particularly with the contact surface 1210*a* of the interfering feature 1210, the interfering feature 1210 is compressed, as shown in FIG. 1(*a*). This contact may create pressure P in the joint component 1200 in and around the interfering feature 1210. The pressure P may result in a bowing or distortion 1202*a* of the surface 1202, for example, as shown in FIG. 1(*a*).

In an additional step, shown in FIG. 1(*b*), heat (or other treatment, e.g., chemical treatment) may be applied to the system 1100 of sufficient temperature and/or degree to partially melt and/or cause flow F of the material in the interfering feature 1210. Such flow F may occur in response to the pressure P of compression of the interfering feature 1210, for example. The flow F may relieve the pressure P and relieve the bowing or distortion 1202*a* of the surface 1202, as shown in FIG. 1(*b*).

FIG. 1(*c*) shows a subsequent stage in the precision fit after the melting, for example, has occurred for some time period. As shown in FIG. 1(*c*) the bowing 1202*a* of the surface 1202 has been substantially decreased by flow F. Moreover, the contact surface 1210*a* between the interfering feature 1210 and the component 1300 has increased. In this and other ways, the redistribution of material from the joint component 1200 may create or enhance a precision fit between the component 1300 and the joint component 1200.

FIG. 1B is a perspective view of an example system in which aspects of the present invention could be utilized in a track in an actuating device. As shown in FIG. 1B, an example chain 100 may be disposed, for example, to slide in a track 110 that is part of an actuation system 300. At one end 125, the example chain 100 may be mechanically coupled to an actuation mechanism, such as a hydraulic control cylinder 200. At another end 120, the chain 100 may be mechanically coupled to a device 130, so that motion of the chain 100 along track 110 in the direction 1000, for example, also moves the device 130 along track 110 in the direction 1000. The chain 100 may include a plurality of joint or link components 140 held together via pins 160 or by another suitable mechanism. Other suitable mechanisms for holding the joint or link components 140 of the chain 100 together may include, but are not limited to: latches, bolts, fastening components and spring or other biasing mechanisms.

Figure 2A:
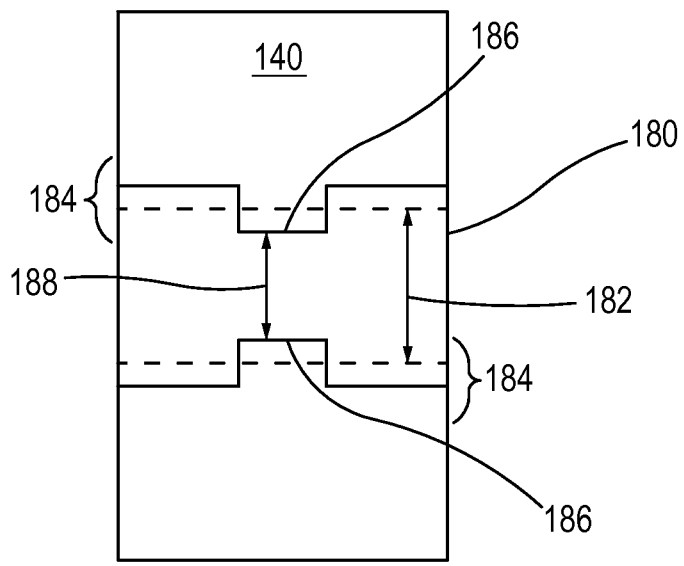
FIG. 2A is a view of an example chain link prior to the installation of a pin and prior to induction heating or other treatment, for use in accordance with aspects of the present invention.
Figure 2B:
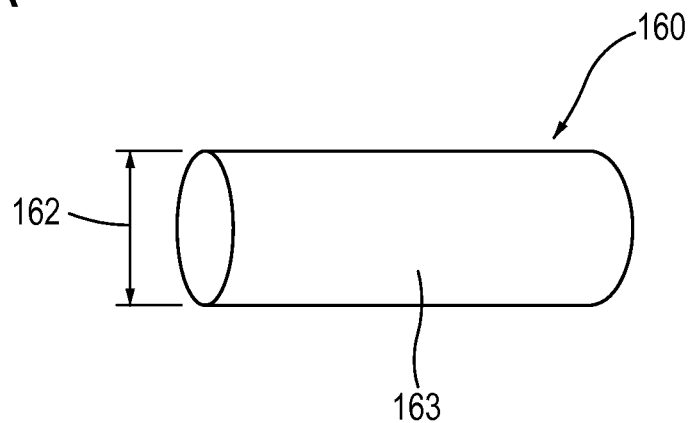
FIG. 2B is a is a perspective view of an example pin prior to the installation of a pin and prior to induction heating or other treatment, for use in accordance with aspects of the present invention.

FIG. 2A is a perspective view of an example joint element 140 prior to the installation of a pin, in accordance with aspects of the present invention. FIG. 2B is a perspective view of an exemplary pin 160 usable in accordance with aspects of the present invention. Certain features, such as rollers 150, are not shown in FIG. 2 in order to more clearly show the mating surfaces of the pin and link. However, it is to be understood that these features, including the rollers 150, may be included in any of the joint or link components 140 described herein. FIG. 3A is a perspective view of an example actuating chain, of the type that might include joints for use in accordance with aspects of the present invention, before the joints are subject to induction heating or other treatment. For clarity, FIG. 3A includes several features not shown in FIG. 2, including rollers 140 and side arms 171, 172 discussed further below.

Chain joint or link components 140 may be fabricated from and include any suitable material, including polymer, ceramic, metal or combinations thereof. Chain joint or link components 140 may also be fabricated from composite materials.

As shown in FIG. 2B, each exemplary pin 160 has a diameter 162 and a mating surface 163. In assembly of the chain, the pin 160 may be inserted into the opening or recess 180 of the joint or link component 140, as further discussed below. Pin 160 may also be fabricated from any suitable material used for the chain links. In certain variations, it is advantageous for the pin 160 to be fabricated from electrically and/or thermally conductive material, such as a metal. Pin 160 may have any suitable shape. For example, pin 160 may have the shape of a cylinder with a circular cross section of diameter 162, as shown in FIG. 2B. Pin 160 may include various other features not shown in FIG. 2B, including grooves, threads, holes or nodules for, among other things, improving the ability to fasten the pin 160 to the chain 100.

As shown in FIGS. 3A and 3B, rollers 150 may be attached to the joint or link components 140 and/or be fixed to the links via one or more pins 160 (FIG. 1B). The rollers 150 generally reduce sliding resistance on the chain 100 in sliding back and forth in direction 1000 along track 110 (FIG. 1B). In some variations, the pins 160 may rotate with the rollers 150 and act as axes for the rollers 150. Rollers 150 may, for example, comprise wheels fabricated from the same or a similar material as, or a different material from, the joint or link components 140.

Rollers 150 may take on other shapes, including spherical or cylindrical shapes. Suitable rollers 150 may be fabricated from polymer or ceramic materials, among others. Other materials suitable for the rollers 150 may include metals, metal alloys and composites. In other variations, chains 100 may include other features instead of, or in addition to, the rollers 150. For example, the chain joint or link components 140 may include a coating that allows the chain to slide on the track 110 with relatively low friction. Such low friction coatings may include a variety of suitable materials, including TEFLON® made by DuPont™ of Wilmington, Del., as well as other low friction materials (e.g., quasicrystalline materials).

As shown in FIG. 3A, chain joint or link components 140 may include a variety of suitable interlocking features that allow interlocking to form a chain 100. For example, as shown in FIG. 3A, chain joint or link components 140 may include one or more side arms 171, 172 that interlock with adjacent chain joint or link components 140. Many variations of side arms 171, 172 are possible. For example, the chain 100 may be configured so that alternate links 141 and 142 in the chain 100, respectively, have exterior arms 171 and interior arms 172. For example, the exterior arms of link 141 may be laterally positioned outward relative to the position of interior arms 172 of adjacent link 142. In this example, the exterior arms 171 and interior arms 172 are configured to interlock, as shown in FIG. 3A, and are fastened together with a pin 160 or other suitable fastening mechanism. Alternatively, the chain 100 could include links with and without side arms 171, 172, alternating with links including one or more type of side arm 171, 172. The links without side arms 171, 172 would then accept the side arms 171, 172 from adjacent chain joint or link components 140. In other cases, each joint element 140 may include alternating side arms 171, 172, such that each individual joint or link component 140 has a single side arm 171, 172 interacting with an adjacent joint or link component 140.

The interlocking mechanism that locks chain joint or link components 140 together via the side arms 171, 172 may include, for example, providing an opening 173 in the side arms 171, 172 for accepting the pins 160. However, it is to be understood than any other suitable fastening or locking system is also possible. For example, the side arms 171, 172 may include a latch that latches onto the joint or link component 140, pin 160 or other component.

Each joint or link component 140 may include an inner wall defining an opening or recess 180 for, among other things, accommodating a pin 160. As shown in FIG. 2A, the outer diameter 182 of the opening or recess 180 may be equal to or slightly larger than the diameter 162 of the pin 160. Alternatively, in other variations, it may advantageous for the outer diameter 182 of the opening or recess 180 to be slightly smaller than the diameter 162 of the pin 160. Material of the joint or link component 140 may be selected such that the force of insertion of the pin 160 causes it to flow and make an improved contact with the pin 160.

As shown in FIG. 2A, the interior surface of the opening or recess 180 includes a mating surface 184 that may be flush with the pin 160 once the pin 160 is inserted into the opening or recess 180. Generally, portions of the mating surface 184 mate with the mating surface 163 of the pin 160 once the pin 160 is inserted into the opening or recess 180. However, substantial portions of the mating surface 184 may be configured such that they do not initially mate directly with the pin 160 and/or can provide a relief or "sink" for displaced or flowing material from a melted or otherwise displaced interfering feature. The mating surface 184 may comprise any of the materials discussed herein. The mating surface 184, for example, may be made of the same as or a similar material to that of the joint or link component 140. Alternatively, it may be advantageous in certain variations for the mating surface 184 to comprise a material with an increased flow (i.e., a softer material) than the material in the remaining portions of the joint or link component 140.

The mating surface 184 may further include an interfering feature or features 186. The interfering feature 186 may protrude from the mating surface 184 sufficiently so that a corresponding portion of an inner diameter 188 of the opening or recess 180 is smaller than the diameter 162 of the pin 160. In this example, inserting the pin 160 into the opening or recess 180 may cause "interference" between the interfering feature 186 of the mating surface 184 and the corresponding surface of the pin 160. By "interference," among other things, it is meant that, upon application of a suitable amount of force, the interfering feature 186 and portions of the pin 160 are forced into close proximity with one another such that they, as nearly as possible, occupy the same space. When this happens, generally the interfering feature 186, the pin 160, or both, may become deformed. Moreover, any deformation of the interfering feature 186, the pin 160, or both, may leave residual stresses in the joint or link component 140 and/or in other components, which may cause a flow of the joint or link component 140 or other component material, upon changing a flow characteristic of the joint or link component 140 material of at least the interfering feature 186, such as if heat (or other treatment) is applied.

The interfering feature 186 may, for example, comprise a single, ring-shaped feature in the center of the mating surface 184, as shown in FIG. 2A. Alternatively, the interfering feature 186 may have other shapes, including multiple rings, zig-zag characteristics, screw thread, or tire tread shapes. In some variations, it may be advantageous for the interfering feature 186 to comprise a single structure in the interior of the mating surface 184, with openings to the exterior of the shaft, so as to allow gas to escape from between the joint or link component 140 and the pin 160 if the application of heat (or other treatment) causes a flow of link material. Allowing such gas flow may, for example, prevent the formation of gas pockets between the joint or link component 140 and the pin 160, or on the mating surface 184 once the pin 160 is placed in the opening or recess 180. Further, gas escape channels may be provided by such features as radial passages, as shown in FIG. 2A. For example, such radial passages may connect the opening or recess 180 to the ambient environment. Additionally the radial passages or other openings may provide areas for the molten material to flow into, which, among other things, may relieve residual compression. Although FIG. 2A shows only a single interfering feature 186, the mating surface 184 of the opening or recess 180 may include multiple interfering features 186. Multiple interfering features 186 or a single interfering feature 186 may, for example, occur in a pattern, such a spiral or screw thread pattern. Patterns, such as spiral patterns, may increase the proportion of the mating surface 184 that is part of the interfering feature 186, while allowing gas flow between the interior of the hole or recess 180 and its exterior 190. Other suitable patterns, for example, may include: checkerboard patterns, tire tread patterns, striped patterns, grid patterns or other patterns. Other possible versions could include no interfering feature (e.g., a thin disc that has a smooth bore, and is thin enough to allow gas and melted material to flow outward, without needing recesses to permit such flow).

In addition, stabilizing mechanisms may be employed either between the joint or link component 140 and the pin 160, between adjacent joint or link components 140 (such as attached to or integrated with arms 171, 172, or between pins 160), or between chain 100 and track 110.

FIG. 3B shows an example stabilization mechanism 181, such as but not limited to a spring (as illustrated) or a damper. Such stabilizing mechanisms can, among other things, dampen vibrations that occur as the chain 100 is used to actuate devices, such as device 130 (FIG. 1B). Multiple springs or other shock absorbing systems are also possible. Other example stabilizing mechanisms include, but are not limited to: spring or other biasing mechanisms, hydraulic shock absorbers, layers of foam and/or other shock absorbing material, layers of soft material, gel layers, gas layers and magnetic levitation devices and features.

Although not exclusively, the chain 100 may be actuated via hydraulic systems, such as the example control cylinder 200 shown in FIG. 1B. In the example of FIG. 1B, the control cylinder 200 includes a shaft 201 that can be mechanically coupled to one end 120 of the chain 100. When hydraulic fluid is pumped into or drawn from the control cylinder 200, such as via connected hydraulic lines, the shaft 201 moves along direction 1000, thereby causing the chain 100 to slide back and forth along the track 110 in direction 1000, as indicated in FIG. 1B. Other actuation mechanisms are also possible. For example, the chain 100 may be actuated by any suitable mechanism including, but not limited to: electric motor, wire/rod, cable, gas propulsion, or other mechanical driver.

Figure 4:
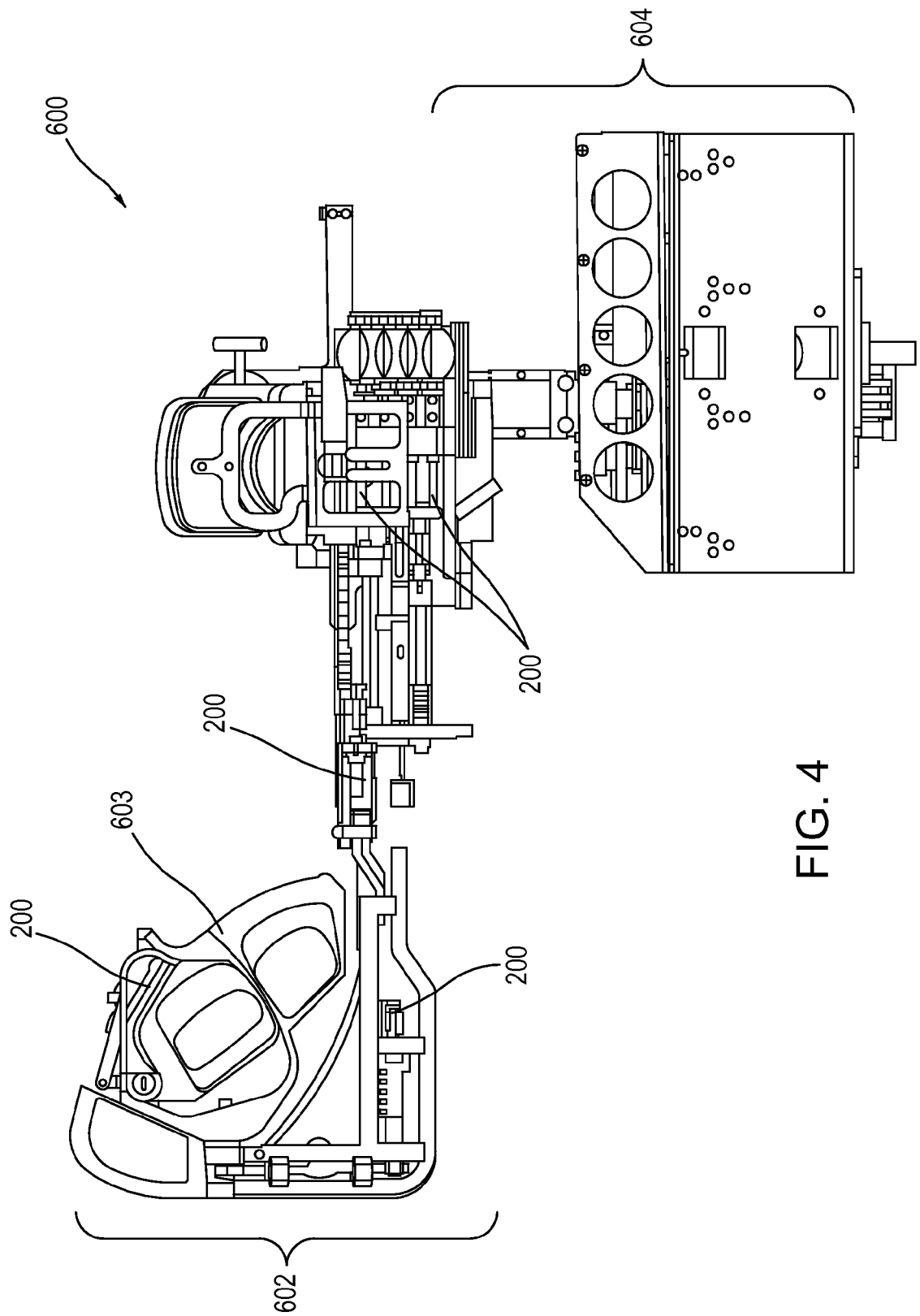
FIG. 4 is a detailed drawing of a side view of one variation of an example control portion that may be used in accordance with aspects of the present invention.

FIG. 4 is a detailed drawing of a side view of one variation of an example control portion 600 that may be used in conjunction with aspects of the present invention. The topmost portion of the control portion 600 contains micro controls 602.

In general, the micro controls 602 may control the micro or relatively-finer motion of aspects of the slave portion. For example, the micro controls 602 may control movements of instruments and/or tools in the slave portion within an operational environment. In contrast, the macro controls 602 shown in FIG. 4 may be used to control macro or relatively coarser motions of the slave portion. For example, the macro controls 602 may be used to actuate the movement of the example chain 100 shown in FIG. 1B in order, for example, to position a device 130. It should be noted that variations of such an example chain 100 are not limited to coarse or macro motions and may also be used in micro motions, such as those actuated by micro controls 602. The terms "macro" or "micro" are not meant to be interpreted literally, specifically or rigorously and merely serve to give a broad understanding of how various aspects of the invention, and related devices, relate to one another.

The control portion 600 shown in FIG. 4 may have other aspects that provide additional degrees of freedom in the motions that may be transmitted from the user to the slave portion of the device. Generally, each degree of freedom may correspond to its own control cylinder 200, as shown in FIG. 4. For example, the user may grasp and move the grasper hand assembly 603 in various directions. These and similar motions may define an input force or motion that generally affect a mechanical response in the control cylinders 120, which transmit the mechanical response to the slave portion of the device via hydraulic lines or other suitable features.

Figure 5:
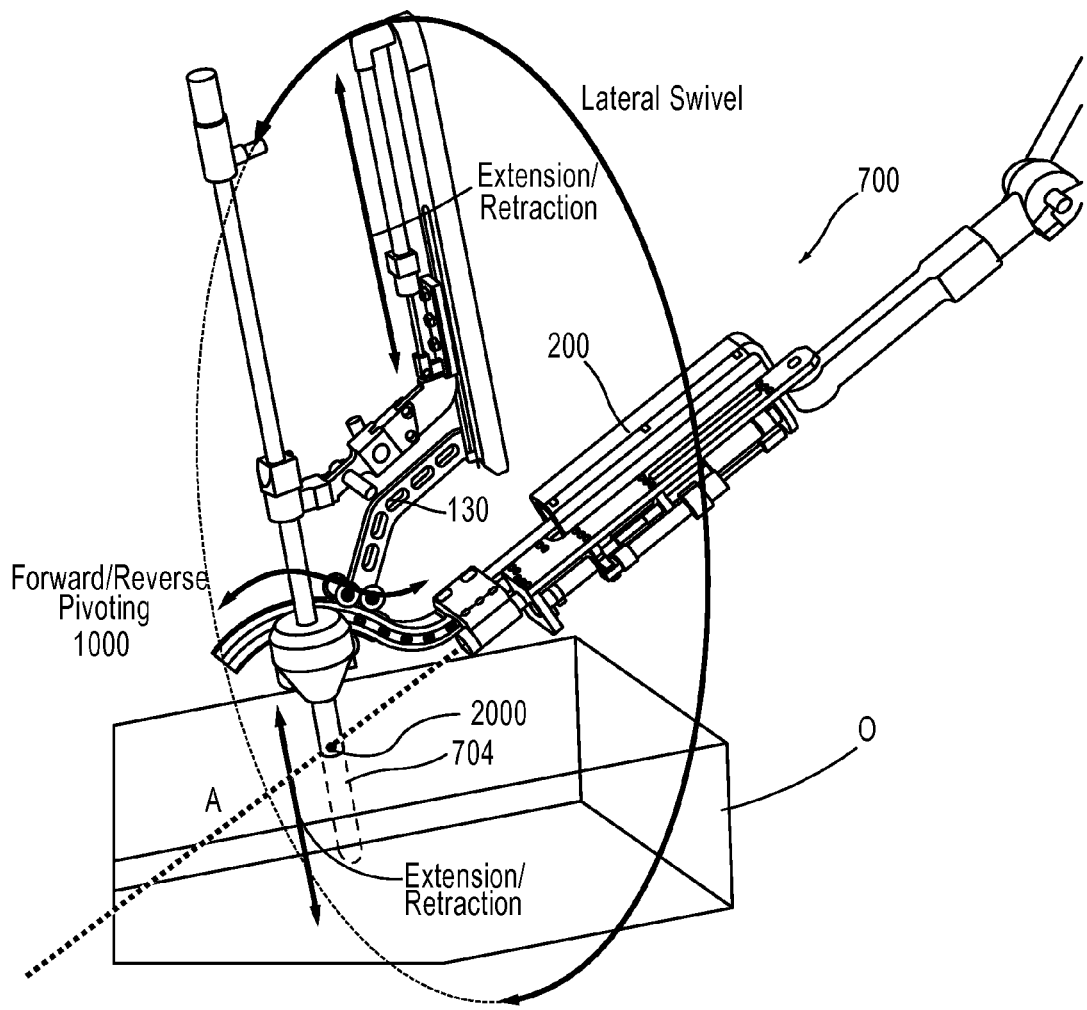
FIG. 5 is an overview of three example macro degrees of freedom in a variation of a slave they may be used in accordance with aspects of the present invention.

FIG. 5 is a detailed drawing of a side view of one variation of a slave portion that might include the chain of FIG. 1B. As shown in FIG. 5, the chain 100 and track 110 of FIG. 1B may be incorporated in a slave portion 700 that includes several additional features. In particular, a tool 704 may be mechanically coupled to the device 130, so that the tool 704 may move with device 130 when it is actuated by the chain 100. The tool 704 may, for example, itself include various other tools (e.g., forceps, scalpels) used in surgery. FIG. 4 also shows the control cylinder 200 of FIG. 1B incorporated into an arm section 702 of the slave portion 700.

FIG. 5 is also an overview of three example macro degrees of freedom in a variation of an example slave portion 700 as they may be used in conjunction with aspects of the present invention. It should be noted that, while the example degrees of freedom are useful for certain applications, they are not meant to be exhaustive. Other degrees of freedom are within the scope hereof. It is therefore possible to modify the existing apparatus as described to encompass either additional or fewer degrees of freedom, as needed. All such modifications should be considered within the scope hereof.

In FIG. 5, one of the example macro degrees of freedom shown is Forward/Reverse Pivoting along direction 1000 of the device 130, tool 704 and related components. Forward/Reverse Pivoting along direction 1000 may be actuated, for example, by motion of the chain 100 along track 110, as shown in FIGS. 1(*a*)-1B and 5 and accompanying description.

Forward/Reverse Pivoting along direction 1000 may allow tool 704 to pivot about a central pivot point, such as Pivot Point 2000 shown in FIG. 5. This particular degree of freedom is useful for, among other things, positioning the tool 704 about a particular area of interest in an operational environment. For example, the Forward/Reverse Pivoting along direction 1000 degree of freedom can be used to position the tool 704, such as a scalpel, in a position appropriate for making an incision. As another example, the Forward/Reverse Pivoting along direction 1000 degree of freedom can be used to position forceps on the end of the tool 704 in a position appropriate for grasping a particular object (e.g., an organ or tissue).

Other example degrees of freedom shown in FIG. 4 (including: Lateral Swivel and Extension/Retraction) each may employ a chain 100 and track 110 system 300, such as that shown in FIG. 1B, for some part of the actuation involved.

Methods of Chain Fabrication

The following is a general description of example methods by which a chain 100, such as shown in FIGS. 1(*a*)-1(*c*), 1B, and 5, may be fabricated. The methods, materials and specific examples discussed herein are meant to be merely illustrative, and not limiting. Any of the steps herein may be omitted or recombined, as appropriate, as needed in accordance with aspects of the invention. The methods may be generally applied to form, fabricate or modify chains made from a variety of suitable materials and as manufactured in a variety of suitable configurations. It is also to be understood that the methods and specific examples are not limited to actuating chains or chains used in remote mechanical actuation. Rather, joints produced as described herein may be used in a variety of suitable contexts and for a variety of suitable purposes, including, but not limited to: rotary or linear bearings, universal joints, and cable guides.

Figure 6:
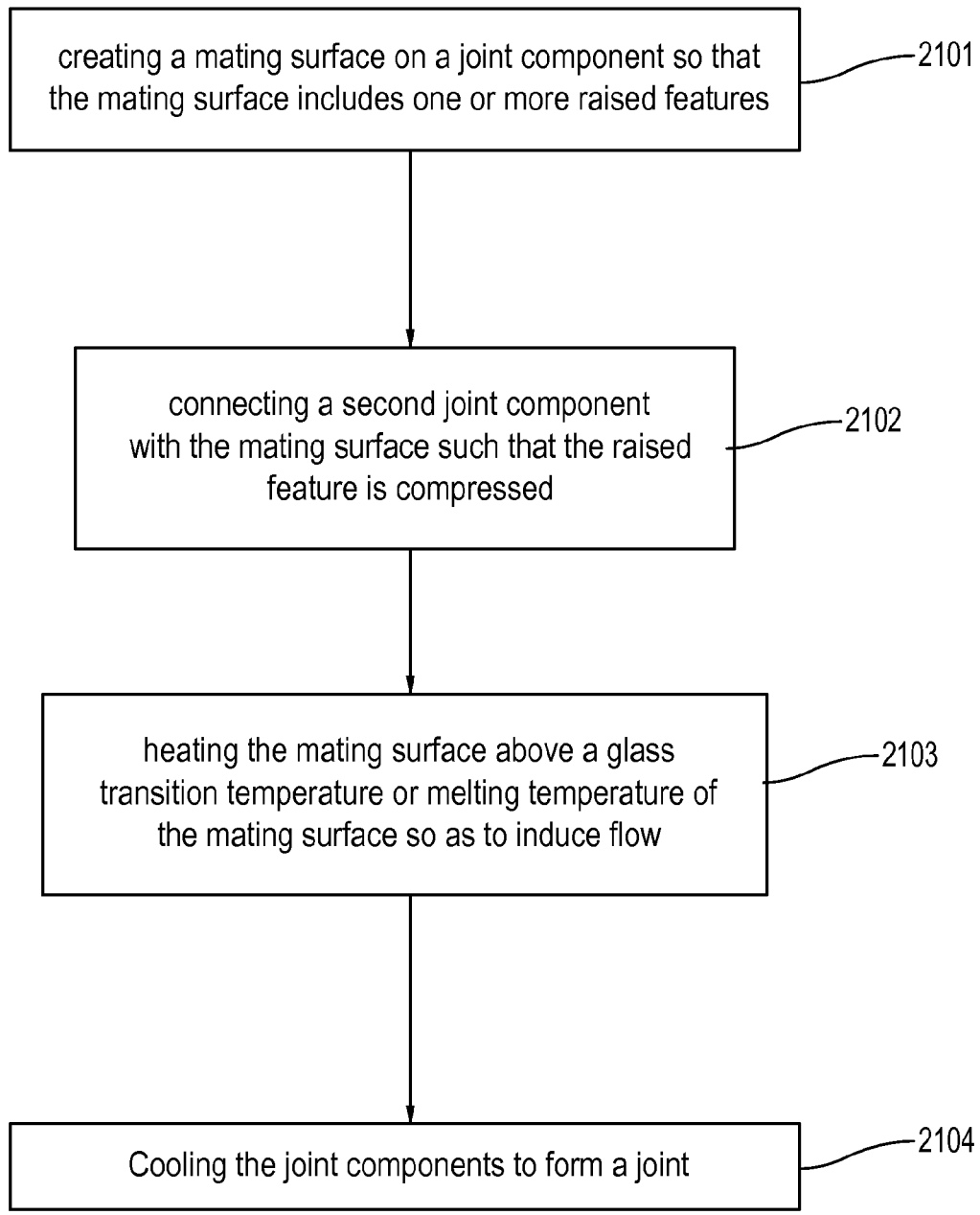
FIG. 6 is a flowchart of an overview of an example method of creating a precision-fit joint, in accordance with aspects of the present invention.

FIG. 6 is a flowchart of an overview of an example method of creating a precision-fit joint, in accordance with aspects of the present invention. In a first step, 2101, a joint component is created. The joint component has a mating surface for mating with another joint component. The mating surface includes at least one interfering feature. In step 2102, a second joint component is connected with the mating surface, such that the interfering feature is compressed. For example, in one aspect, the first joint component with the raised surface may be a link, such as joint or link component having a mating surface, and the second joint component may be a pin, or vice versa. Alternatively, the first and second joint components may be any type of joint components. Generally, the connection between components can be accomplished by inserting the pin, for example, or other fastening component, into the joint or link component, such that the pin or other fastening component connects with and causes the compression of the interfering feature. Fitting in this way to cause compression of the interfering feature may be referred to as "interference fitting."

In step 2103, heating or other energy transfer or similarly acting treatment is performed. For example, the interfering feature of the mating surface may be heated above a flow temperature Tf (e.g., a glass transition temperature or melting temperature) of the material of the joint component, so as to induce flow of material from the interfering feature to an area between the mating surface and the pin, such as an area of low pressure to, among other things, relieve the interference stresses between, for example, the mating surface on the joint or link component and a corresponding surface of the pin or other fastening component. Heating may be accomplished by induction heating, among other methods, for example.

Finally, in step 2104, the joint components are cooled to below the flow temperature Tf. This cooling stops flow of the material and creates a working joint having a precision fit between the two joint components.

For example, in one exemplary implementation, referring to FIG. 2A, an example joint element 140 prior to the installation of a pin and prior to induction heating includes an internal wall defining a shaft sized for receiving a pin. The internal wall may also be referred to as the mating surface, and the mating surface may further include an interfering feature sized to interfere with the pin upon insertion, thereby causing deformation of the interfering feature. To assemble a chain, such as the chain of FIGS. 3A and 3B, each of the joint or link components 140 in the chain 100 are assembled prior to "interference fitting" the pins 160. For example, the joint or link components 140 may be aligned so as to form the chain 100 shown in FIGS. 3A and 3B. Although it is possible to perform the assembly of the chain 100 in the track 110, it is generally not necessary to do so. The chain may be assembled separately from the track 110, for example, and inserted subsequently into the track 110. The process of "interference fitting" is described further below.

Figure 7:
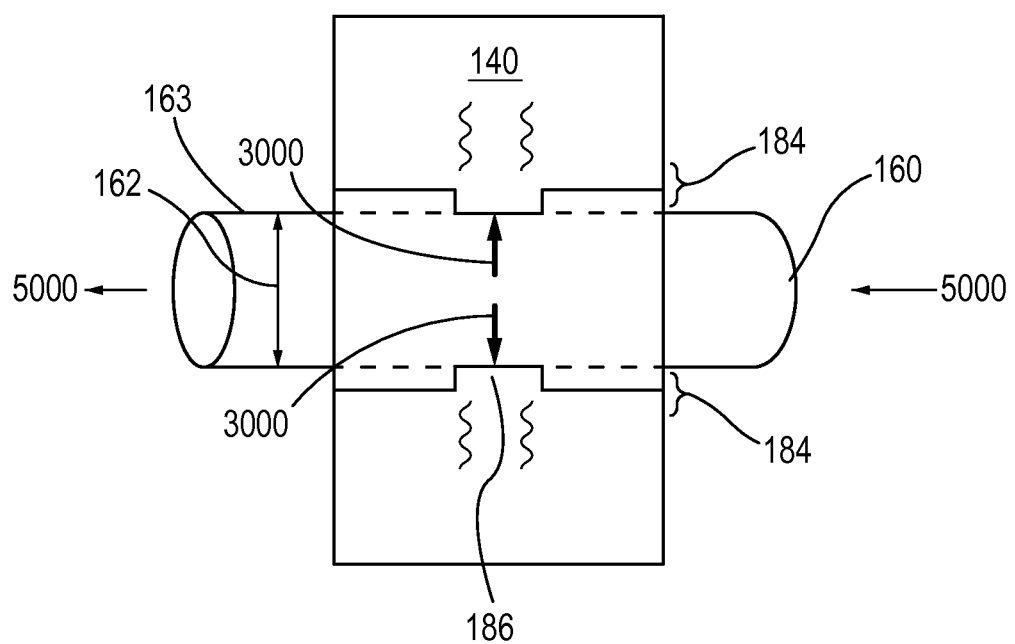
FIG. 7 is a perspective view of the example chain link of FIG. 4 after pin installation but prior to induction heating or other treatment, in accordance with aspects of the present invention.

FIG. 7 is a perspective view of the example chain link of FIG. 4 after pin installation but prior to induction heating. Pins 160 are inserted into opening or recess 180. Certain features, such as rollers 150, are not shown in FIG. 7 in order to more clearly show the mating surfaces of the pin and link. However, it is to be understood that these features, including the rollers 150, may be included in any of the joint or link components 140 described herein.

Generally, the inner diameter 188 of the opening or recess 180 may be smaller than the diameter 162 of the pin 160. In this case, inserting the pin 160 into the opening or recess 180 may require forcing portions of the joint or link component 140, and more specifically the mating surface 184 of the link (e.g., the interfering features 186), out of the way of the pin 160. Alternatively, the inner diameter 188 of the joint or link component 140 may be larger than the diameter 162 of the pin 160. In this case, the pin 160 is inserted into the opening or recess 180 and a compressive force is applied, such that a raised or other portion of the mating surface 184 of the joint or link component 140 is pressed against the pin 160. In either case, whether the inner diameter 188 of the link is larger or smaller than the diameter 162 of the pin 160, generally sufficient force is applied so that, in some cases, portions of the mating surface 184 contact the pin 160 on its mating surface 163. Typically, the interfering features 186 of the mating surface 184 contact the pin 160 and are compressed against the mating surface 163 of the pin 160, with compressive force 3000, as shown in FIG. 7.

Figure 8:
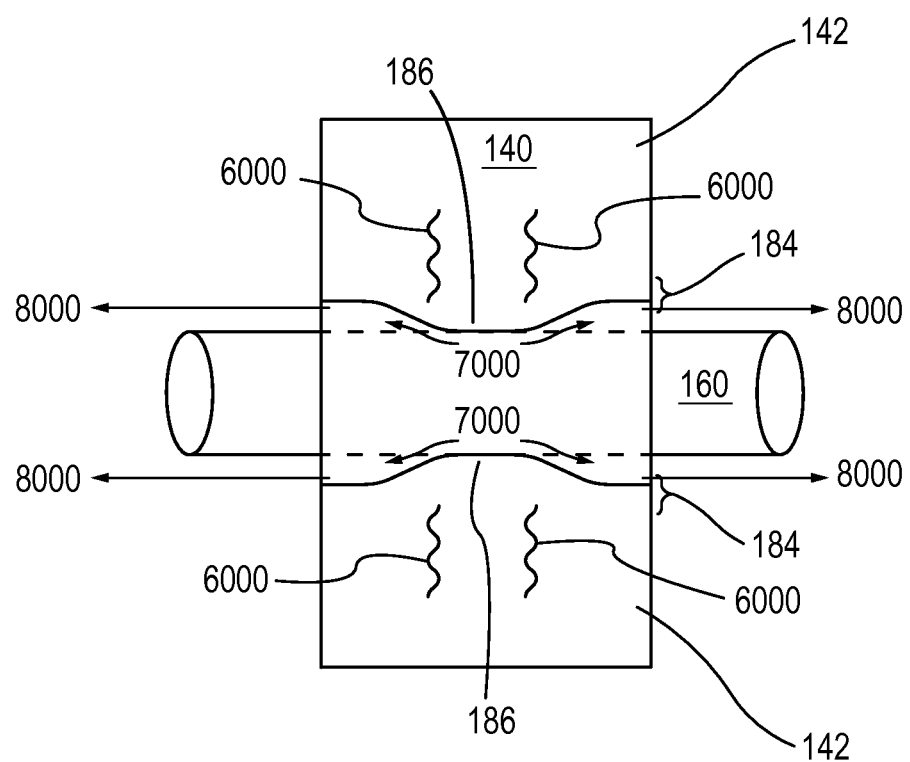
FIG. 8 is a perspective view of the example chain link of FIG. 7 during induction heating or other treatment, in accordance with aspects of the present invention.

FIG. 8 is a perspective view of the example chain link of FIG. 7 during induction heating or other thermal or chemical treatment. Certain features, such as rollers 150, are not shown in FIG. 8 in order to more clearly show the mating surfaces of the pin and link. However, it is to be understood that these features, including the rollers 150, may be included in any of the joint or link components 140 described herein.

When the joint or link component 140 is mated with the pin 160, the interfering feature 186 may be compressed against the mating surface 163 of the pin 160, as shown in FIGS. 6 and 7. Electric or inductive currents 5000, for example, may then be introduced into the pin 160 as the compression forces 3000 are applied. Generally, the pins 160 may comprise material with a substantial electrical resistance, such that the electric or inductive currents 5000 cause resistive or inductive heating of the pin 160. The pins 160 may also be heated directly using heating by conduction or convection, where convection may include, for example, heating the pins 160 in the blast of hot air gun and, subsequently, inserting each pin into a plastic part.

The pins 160 may also be formed of multiple components that include resistive heating elements. Such resistive heating elements may be positioned near the mating surface 163 of the pin 160. Use of resistive heating elements may decrease the energy required to fabricate the chain and/or reduce problems associated with eddy currents and unintentional heating of the pin 160 and/or joint or link component 140 system, among other things. Use of resistive heating elements may be especially advantageous in avoiding heating damage to sensitive components or portions of components, such as the rollers 150, for example. Resistive or induction heating of pin 160 can then be performed, generating heat flow 6000 into the surrounding joint or link component 140.

Temperature elevation, Te, in the joint or link component 140, which may be induced by the heat flow 6000, for example, will depend on the resistive properties of the pin 160, as well as the magnitude of the currents 5000 applied, among other factors. In general, however, it is advantageous for the temperature elevation, Te, induced by the heat flow 6000 in the joint or link component 140 to be substantially higher than a phase transition or flow temperature, Tf, of the material of the joint or link component 140. The phase transition or flow temperature, Tf, of the joint or link component 140 may be, for example, a glass transition temperature or a melting temperature if the joint or link component 140 includes a polymeric material. Heating the joint or link component 140 including, for example, at least the interfering feature 186 of the mating surface 184, above the flow temperature Tf may induce flow and deformation of the material of joint or link component 140.

The heat flow 6000 may cause a local heating of the joint or link components 140 in and around the mating surface 184 that contacts the mating surface 163 of the pin 160. In such event, temperature elevation Te may principally take place in the interfering features 186 of the mating surface 184, while minimal or less heating may occur in other portions of the joint or link component 140. If the temperature elevation Te is local to the interfering features 186, for example, less or minimal heat-induced deformation of the joint or link component 140 may occur in portions of the link 140 that are relatively distant from the pin 160. Localizing the heat-induced deformation to portions of the mating surface 184 may be advantageous, for example, in order to preserve the structural integrity of the joint or link component 140 and various features of the link (e.g., to preserve the structural integrity of connections between arms 171, 172 or other linking features, as well as the rollers 150). Localizing the heat-induced deformation to portions of the mating surface 184 may be accomplished by, among other things, constructing the joint or link components 140 so that the thermal conductivity of the joint or link components 140 is relatively low. For example, decreasing the thermal conductivity of the joint or link components 140 may be accomplished by including layers of thermally insulating material in the joint or link components 140, among other methods.

Although resistive heating or other treatment is described in the context of an "interference fit," as described above, it is to be understood that this technique may be applied even in the absence of compression 3000 or an interference fit, as described above. In addition, resistive, or other heating, for example, of the joint or link components 140, pins 160 and other components of the chain 100 may be performed at other stages in chain fabrication in order to, among other things, create more precise fitting among the joint and/or link components 140, pins 160 and other components of the chain 100. Moreover, resistive heating may be applied to seal or connect the joint or link components 140, pins 160 and other components of the chain 100 (e.g., may be applied to fasten arms 171, 172, as described above). Resistive, or other, heating of the chain 100 need not be uniform. In particular, it may be advantageous to heat certain portions of the chain 100 (e.g., mating surface 184, interfering features 186, arms 171, 172) to temperatures in excess of temperatures in other portions of the chain 100 during the heating process. Also, features such as grooves may be formed into higher melting point components to fix such components relative to lower melting point components As shown in FIG. 8, the heat flow 6000 may raise the joint or link component 140 temperature above the flow temperature Tf and, as a consequence, induce a joint or link component 140 material flow 7000 of the joint or link component 140 material in and around the pin 160. The joint or link component 140 material flow 7000 may redistribute material in the interfering features 186 in and around the mating surface 163 of the pin 160 in such a way to create a better fit between the joint or link component 140 and pin 160. In particular, compressive force 3000 may increase and direct the joint or link component 140 material flow 7000 such that the flow 7000 tends to fill gaps, spaces or bubbles between the mating surface 184 of the joint or link component 140 and the mating surface 163 of the pin 160. During this process, gas 8000 from the gaps, spaces or bubbles between the mating surface 184 of the joint or link component 140 and the mating surface 163 of the pin 160 may exit the joint or link component 140.

Figure 9:
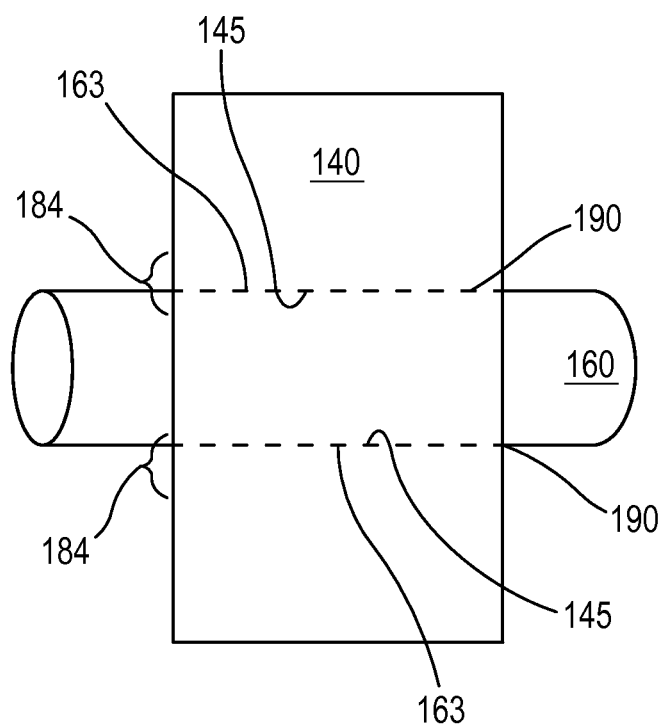
FIG. 9 is a perspective view of the example chain link of FIG. 8 after heating or other treatment, when the interface between the pin and the link is precise fit, in accordance with aspects of the present invention.

The joint or link component 140 material flow 7000 ultimately contributes to the fit interface 190 between the joint or link component 140 and pin 160 shown in FIG. 9. FIG. 9 is a perspective view of the example chain link of FIG. 8 after heating, when the interface between the pin and the link is precise fit. Certain features, such as rollers, are omitted in FIG. 9, in order to more clearly show the mating surfaces of the pin and link. However, it is to be understood that these features, including the rollers, may be included in any of the joint or link components 140 or other components, such as rotary or linear bearings, u-joints, etc., described herein.

Once material flow 7000 has occurred, generally the electric or inductive currents 5000, for example, are stopped, resulting in a decrease of heat flow 6000 and a decrease in the elevation temperature Te of the mating surface 184. As the temperature of the mating surface 184 decreases below the flow temperature Tf of the joint or link component 140 material, joint or link component 140 material flow 7000 ceases and leaves a precise fit interface 190.

FIG. 10A is a first view and FIG. 10B is a second view of an example chain after induction heating or other treatment. The precise fit interface 190 may, as shown in FIG. 9, result in contact between the mating surfaces of the joints and/or links and/or pins. However, in other variations, the precise fit interface may occur only at one or more portions of the mating surfaces, such that one or more other portions of the mating surfaces are not in contact.

A precision fit between portions of the joint or link component 140 and pins 160, as shown in FIGS. 10A and 10B, may create an interface between the joint and/or link component 140 and/or pin 160, having no gaps or having reduced gaps, thereby resulting in less backlash. Generally, the precision fit may still allow the pins 160 to rotate relative to the joints/links, e.g. defining an interface that allows relative sliding motion, such as in direction 9000 shown in FIG. 10B, in order to reduce resistance for the chain in sliding along a track, such as track 110 shown in FIG. 1B. In this and other ways, for example, the pins 160 may act as axes for rollers in such components, even after the precision fit. However, decreasing the gaps, spaces or bubbles between the mating surface of the joint or link component 140 by creating the precision fit may prevent or greatly reduce movement of the pins 160 in directions other than direction 9000, e.g. in directions approximately normal and/or oblique to the mating interface. Movement in directions other than direction 9000 generally results in backlash between ends of the chain upon actuation, e.g., between control cylinder 200 and device 130 in FIG. 1B. Such backlash can result in potentially damaging imprecise actuation of the device 130, as described above.

It should be noted that the method of heating need not be limited to resistive heating of the pins (e.g., by introducing electric or inductive currents). Any suitable heating mechanism may be used. For example, a heat gun or other external source of heat may be located proximal to and used to heat the pin. If the pin is made from material that is substantially thermally conductive, such as a metal or metal alloy, heat flow may occur as a result of applying or directing external sources of heat to the pins in a substantially similar manner as described for resistive heating above. Similarly, heat flow due to thermal conductivity may cause joint and/or link component material flow for the joint and/or link component so as to create a precision fit therebetween, in a substantially similar manner as described above. In addition, the pins could be pre-heated then pressed into a lower melting point component, for example.

In addition to the compressive force discussed above, external pressure may also be applied to the links during heating in order to, among other things, enhance flow of the material in the interfering features of the mating surface. This pressure may be applied through the use of external force imposing components, such as presses, clamps, vices, and/or other force-applying mechanisms. This pressure may also be, for example, applied uniformly or hydrostatically, such as, may be confined in a pressure chamber. Other suitable devices and methods of applying pressure may also be employed.

Figure 11:
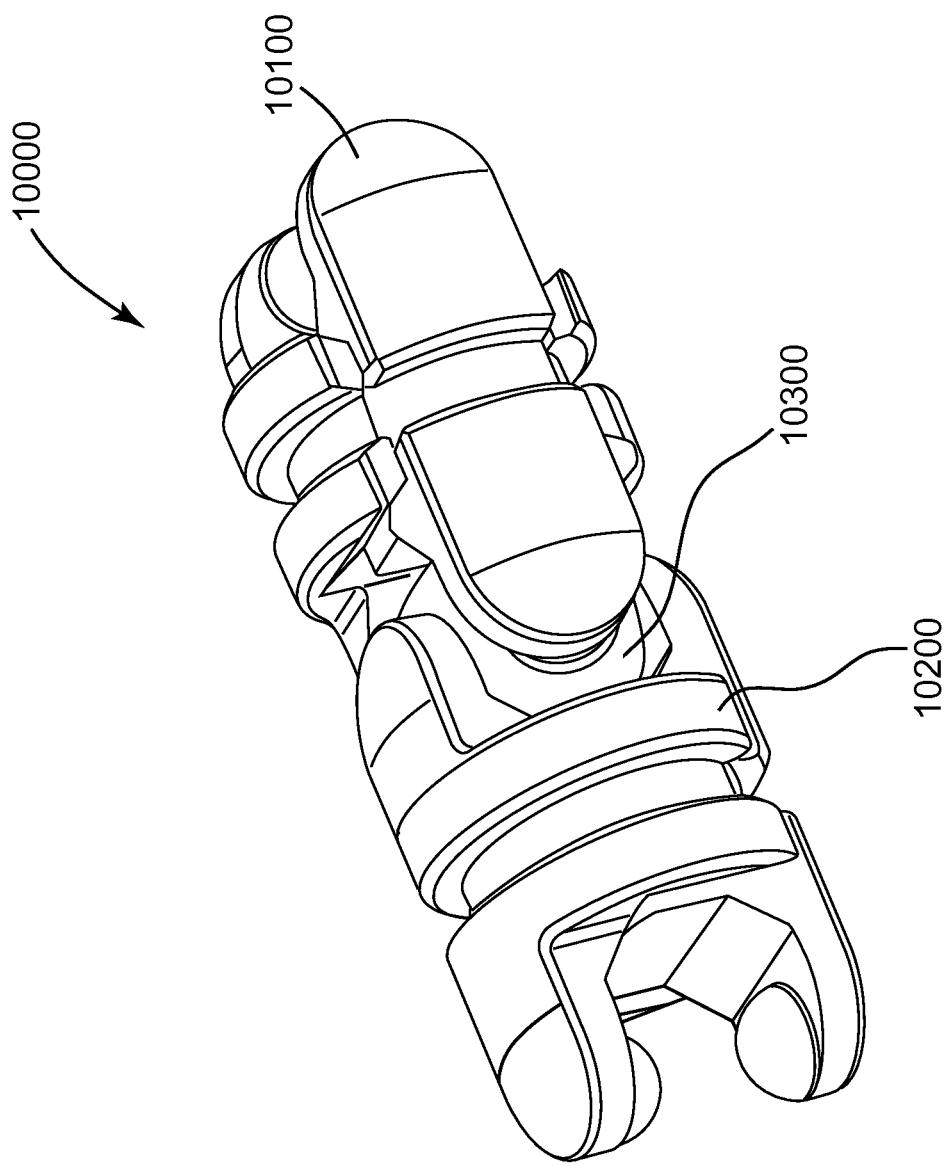
FIG. 11 is a perspective view of another example system that may be used in accordance with aspects of the present invention.
Figure 12:
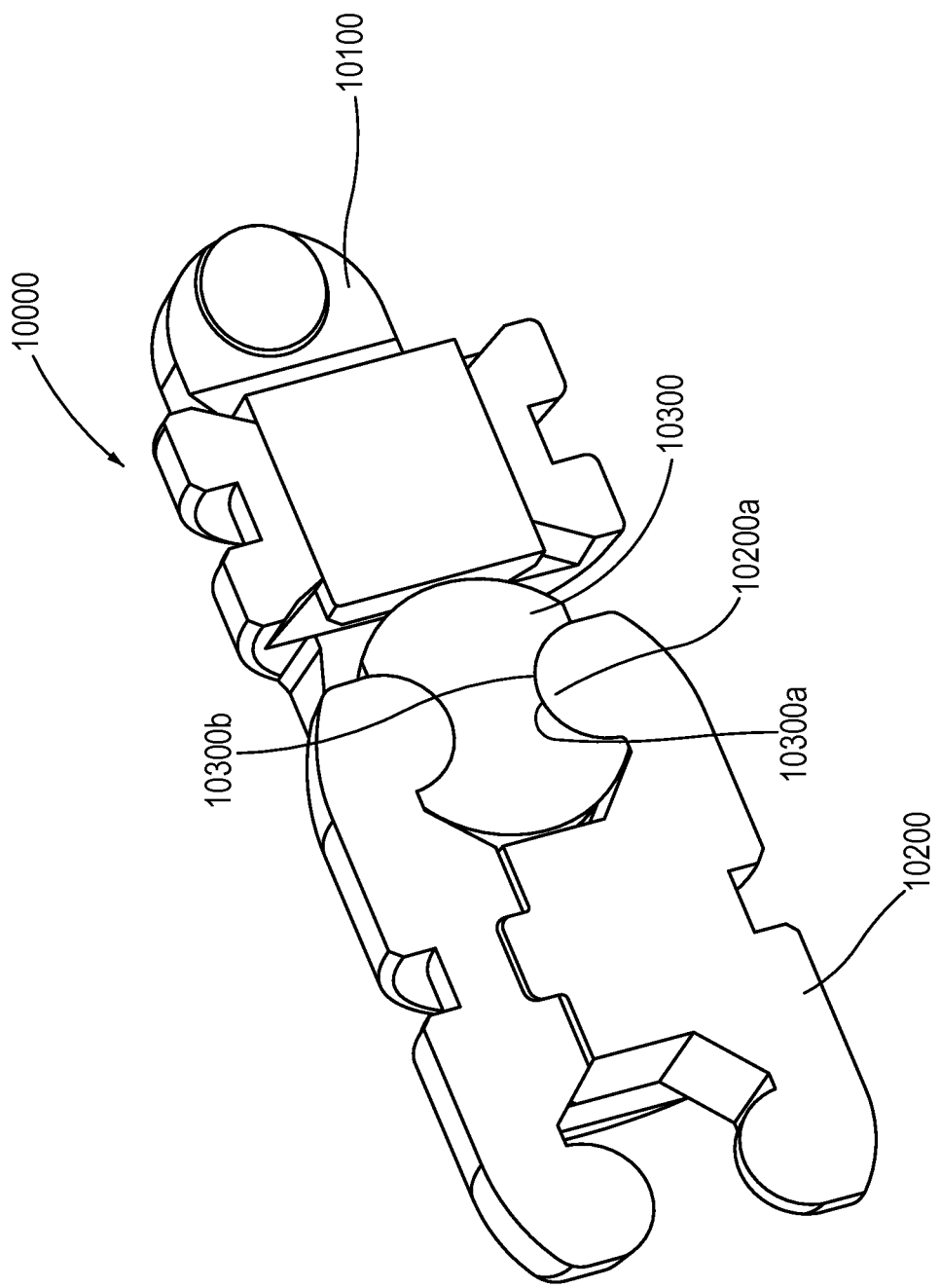
FIG. 12 is a cutaway view of the example system of FIG. 11.
Figure 13:
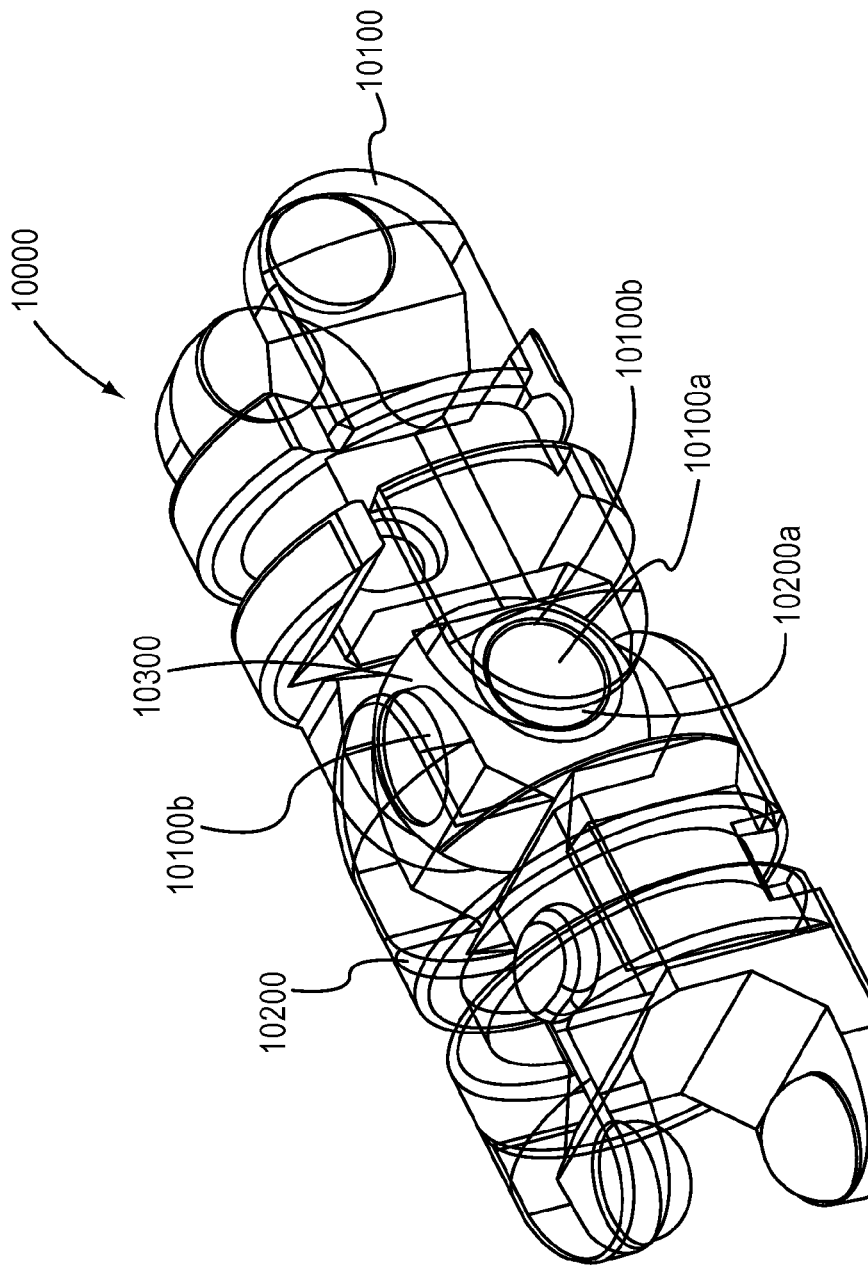
FIG. 13 is a partially transparent view of the example system of FIG. 11.
Figure 14:
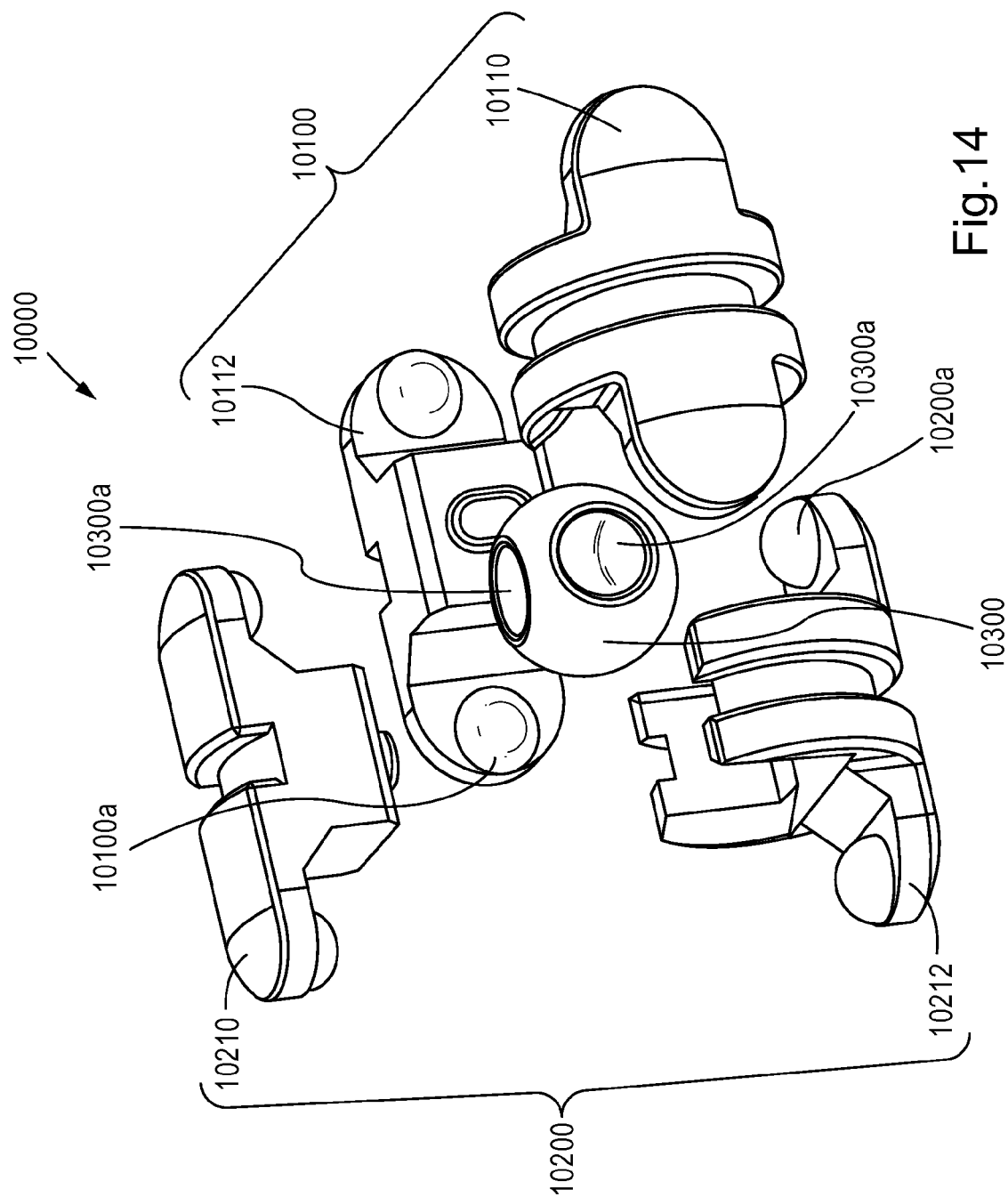
FIG. 14 is an exploded view of the example system of FIG. 11.
Figure 15:
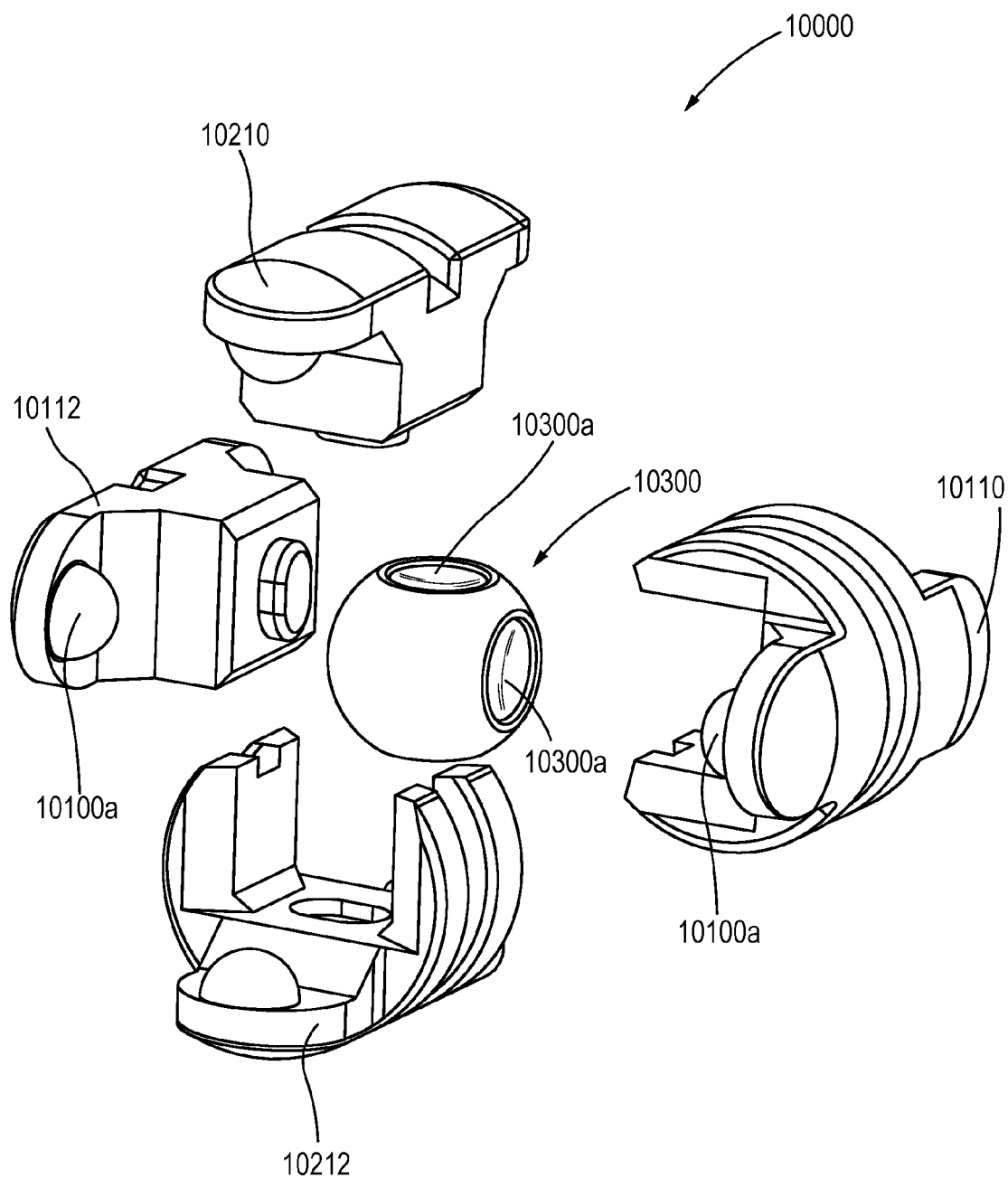
FIG. 15 is another exploded view of the example system of FIG. 11.

FIG. 11 is a perspective view of another example system that may be used in conjunction with aspects of the present invention. FIG. 12 is a cutaway view of the example system of FIG. 11. FIG. 13 is a partially transparent view of the example system of FIG. 11. FIGS. 14 and 15 are exploded views of same.

As shown in FIGS. 11-15, the example system 10000 may include, for example, components 10200 and 10100 that mate or engage a joint component 10300. Such a system 10000 may be used, for example, in joints and/or in devices for remote actuation, such as those used in remote or robotic surgeries. The joint component 10300 may be substantially in the shape of a sphere or partial sphere, or exhibit another suitable shape.

Figure 16:
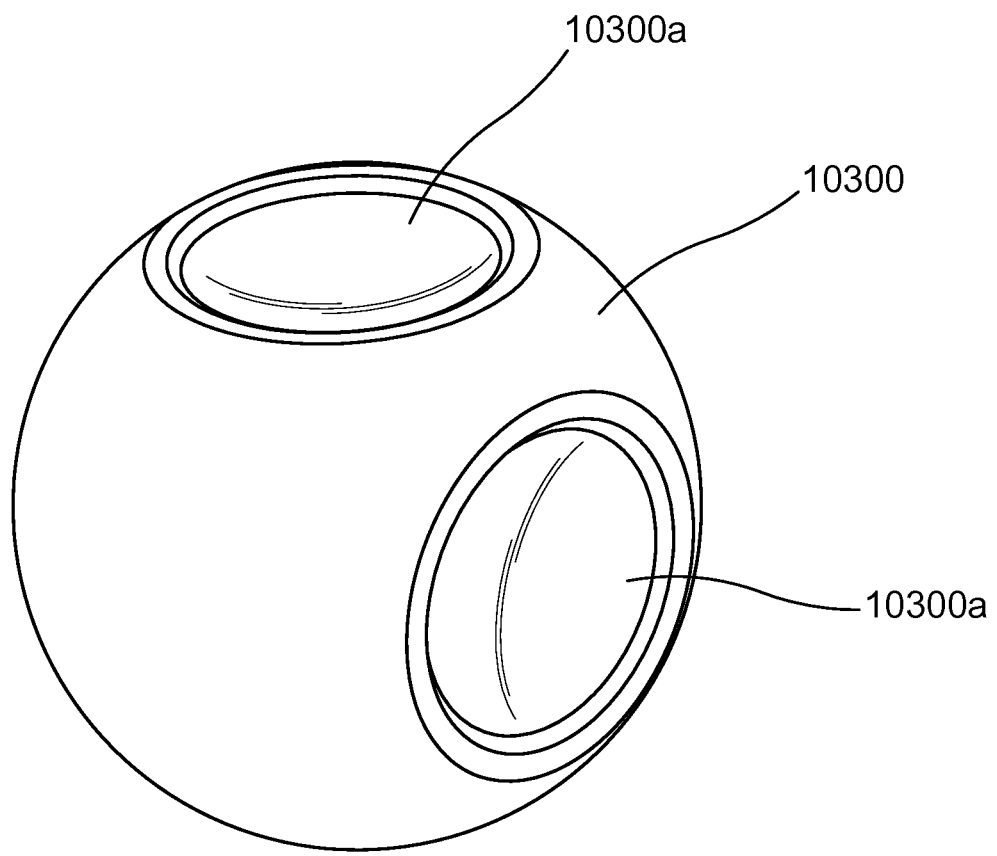
FIG. 16 is close-up view of a component of the example system of FIG. 11.
Figure 17:
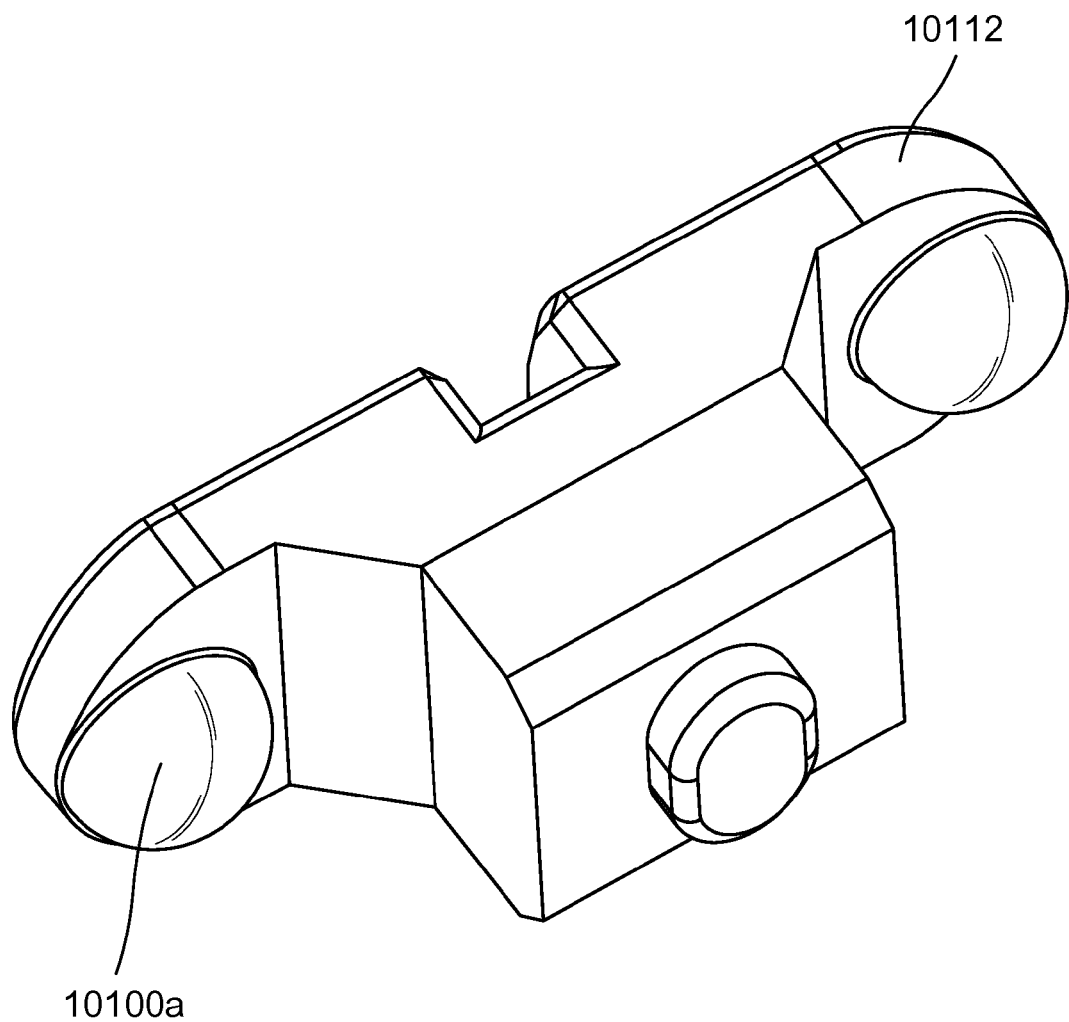
FIG. 17 is close-up view of another component of the example system of FIG. 11.
Figure 18:
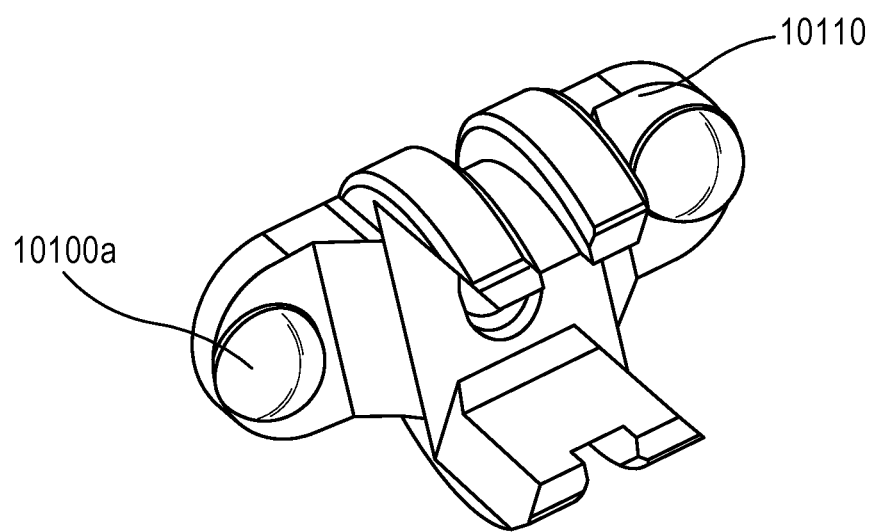
FIG. 18 is close-up view of another component of the example system of FIG. 11.

FIG. 16 is a close-up view of the joint component 10300 of FIGS. 11-15. FIG. 17 is a close-up view of a portion 10112 of the component 10100 of FIGS. 11-15. FIG. 18 is a close-up view of a portion 10110 of the component 10100 of FIGS. 11-15.

As shown, for example, in FIGS. 12 and 13, joint component 10300 may have at least one mating surface 10300*a* which may include interfering feature 10300*b*. In this example, joint component 10300 may comprise a material, for example, with a relatively low melting point (e.g., polymer, polymer composite or like material).

As shown in FIG. 15, for example, component 10100 may further include complementary interlocking components 10110 and 10112. Interlocking components 10110 and 10112 themselves may include mating surfaces 10100*a* for mating with mating surfaces 10300*a* of the joint component 10300. Component 10200 may further include complementary interlocking components 10210 and 10212. Interlocking components 10210 and 10212 may further include mating surfaces 10200*a* for mating with mating surfaces 10300*a* of the joint component 10300. One exemplary method of assembling the system 10000, may include locking interlocking components 10110 and 10112 and locking interlocking components 10210 and 10212 around the joint component 10300, so that mating surfaces 10100*a* and 10200*a* mate with the mating surface 10300 (see, e.g., FIGS. 13 and 14).

In the exemplary implementation of FIGS. 11-15, components 10200 and 10100 may be pressed against joint component 10300, by, for example, clasping interlocking components 10210 and 10212 and clasping interlocking components 10110 and 10112 around joint component 10300. Generally, the mating surfaces 10100*a* and 10200*a* may be mated with the mating surface 10300*a* of the joint component 10300, as shown in FIGS. 12 and 13, for example, as interlocking components 10210, 10212, 10210 and 10212 are locked to one another and around joint component 10300. The resultant assembled configuration is shown in FIG. 11.

FIG. 12 shows an interfering feature 10300*b* included on mating surface 10300*a* of the joint component 10300. Any or all of the mating surfaces 10100*a*, 10200*a* and 10300*a* may include one or more interfering features. In each case, the interfering feature or features may function similarly as the interfering features shown and describes with respect to FIGS. 1(*a*)-1(*c*).

More specifically, locking interlocking components 10210, 10212, 10210 and 10212 to one another and around joint component 10300 to form the component of FIG. 12, may corresponds to one stage of precision fitting similar to as shown and described with respect to FIG. 1(*a*). In this stage, pressure may be applied to portions of the system, or such pressure may be applied to the entire system. For example, mating surfaces 10100*a*, 10200*a* and 10300*a* may be brought into contact. Any interfering feature, such as interfering feature 10300*b*, may be fashioned so that when mating surfaces 10100*a*, 10200*a* and 10300*a* are brought into contact, the interfering feature 10300*b* is compressed, similar to as shown and described for interfering feature 1210 with respect to FIG. 1(*a*). This approach may create pressure in the joint component 10300 and/or the other components 10100 and 10200 in and around the interfering features. The pressure may result in a bowing or distortion of mating surfaces 10100*a*, 10200*a* and 10300*a*, similar to as shown and described for surface 1202 with respect to FIG. 1(*a*).

In an additional step, heat (or other treatment, e.g., chemical treatment) may be applied to the system 10000 of sufficient temperature and/or degree to partially melt and/or cause flow of the material in the interfering feature 10300*b*, similarly to as shown and described for interfering feature 1210 with respect to FIG. 1(*b*). Such flow may occur in response to the application of pressure of compression of the interfering feature 10300*b*. The flow may thereby relieve the pressure and relieve the bowing or distortion of mating surfaces 10100*a*, 10200*a* and 10300*a*, similarly to as shown and described for surface 1202 with respect to FIG. 1(*b*).

Another stage in the assembly process may occur after the melting and flow has proceeded for some time period. In this stage, the bowing or distortion of the mating surfaces 10100*a*, 10200*a* and 10300*a* may substantially decrease as a result of the flow, for example. Moreover, the mating surfaces 10100*a*, 10200*a* and 10300*a* may adhere to a greater extent than absent interference fit, and contact surfaces between the interference features and the mating surfaces 10100*a*, 10200*a* and 10300*a* may have grown, relative to such contact absent interference fit. In this and other ways, the redistribution of material from the joint component 10300 or from other components 10100 and 10200 may create a precision fit between the joint component 10300 and other components 10100 and 10200.

FIGS. 19(*a*) to 19(*f*) contain partial cutaway views of portions of various exemplary features of another system that may be implemented in accordance with aspects of the present invention. FIGS. 19(*a*)-19(*c*) show various aspects of the system 11000 prior to heat or other similarly functioning treatment (e.g., similarly to as shown and described for system 1100 with respect to FIG. 1(*b*). FIGS. 19(*d*)-19(*f*) show various aspects of the system 11000 after heat or other treatment (e.g., similarly to as shown and described for system 1100 with respect to FIG. 1(*b*). FIGS. 19(*a*) and (*d*) are side overviews of portions of the example system 11000 FIGS. 19(*b*) and 19(*e*) are cutaway profiles of the portions of FIGS. 19(*a*) and (*d*), respectively. FIGS. 19(*c*) and 19(*f*) are close-up views of the areas labeled "G" and "W" in FIGS. 19(*b*) and 19(*e*), respectively.

As shown in FIGS. 19(*a*) to 19(*f*), the system portions 11000 may include a shaft 11300, which may comprise metal, for example, and a roller 11200, which may comprise polymer, for example. System portions 11000 may be used, for example, in joints and/or in devices for remote actuation, such as those used in remote or robotic surgeries.

As shown in FIGS. 19(*b*) 19(*c*), 19(*e*) and 19(*f*), roller 11200 may have a mating surface 11200*a* that may include an interfering feature 11200*b*, similar to interfering feature 1210 shown and described with respect to FIGS. 1(*a*)-1(*c*). In this example, roller 11200 may comprise a material, for example, with a relatively low melting point (e.g., polymer, polymer composite or like material). The roller 11200 may have, for example, a doughnut or annular shape so as to accommodate the shaft 11300 in the interior or opening of the roller 11200, as shown in the cutaway view in FIG. 19(*b*), for example. Shaft 11300 may include an interior recess 11300*a*, as shown in FIG. 19(*b*). The shaft 11300 may include a mating surface 11300*b* for, among other things, mating with the mating surface 11200*a* and the interfering feature 11200*b* of the roller 11200.

The shaft 11300 may be, for example, inserted into the roller 11200, as shown in FIG. 19(*a*). In this example, the mating surface 11300*b* of such that the shaft 11300 mates with the mating surface 11200*a* of the roller 11200, as shown in FIG. 19(*b*). The resultant configuration is shown in FIG. 19(*a*).

FIGS. 19(*b*) 19(*c*), 19(*e*) and 19(*f*) show, in part, an interfering feature 11200*b* included on mating surface 11200*a* of the roller 11200. The mating surface 11300*b* of the shaft 11300 may also include one or more interfering features. Such interfering feature or features may function similarly to the interfering feature 1210 shown and described with respect to FIGS. 1(*a*)-1(*c*).

Inserting the shaft 11300 into the roller 11200 is similar to the first stage of precision fitting shown in FIG. 1(*a*). In this stage, pressure may be applied to only small portions of the system, or may be applied to the entire set of system portions shown, for example. In the first stage, mating surfaces 11300*b* and 11200*a* are brought into contact. An interfering feature, such as interfering feature 11200*b*, may be fashioned so that when mating surfaces 11300*b* and 11200*a* are brought into contact, the interfering feature 11200*b* is compressed (FIGS. 19(*b*) and 19(*c*)), similarly to as shown and described for interfering feature 1210 with respect to FIG. 1(*a*). This contact may create pressure P in the roller 11200 and/or the shaft 11300 in and around the interfering features, similar to that shown and described in conjunction with FIG. 1(*b*). The pressure P may result in a bowing or distortion D of mating surfaces 11200*a* (FIGS. 19(*b*) and 19(*c*)), for example, similarly to as shown and described for surface 1202 with respect to FIG. 1(*a*).

In another step, heat (or other treatment, e.g., chemical treatment) may be applied to portions of the system 11000 of sufficient temperature and/or degree to partially melt and/or cause flow of the material in the interfering feature 11200*b*, similarly to as shown and described with respect to interfering feature 1210 in FIG. 1(*b*). Such flow may occur, for example, in response to the pressure P and compression of the interfering feature 11200*b*. The flow may relieve the pressure P and relieve the bowing or distortion D of mating surfaces 11200*a* (FIGS. 19(*b*) and 19(*c*)), for example, similarly to as shown and described with respect to surface 1202 in FIG. 1(*a*).

Another stage in the precision fit process may occur after the melting and flow has proceeded for some time period. In this stage, the bowing or distortion D of mating surface 11200*a* (FIGS. 19(*b*) and 19(*c*)), may have been decreased by some flow amount, similar to as shown and described with respect to interference feature 1210 in FIG. 1(*c*). The result is shown in FIGS. 19(*e*) and 19(*f*). The adherence of mating surface 11200a to the mating surface 11300b of the shaft may be increased, and contact surfaces between the interference features and the mating surfaces may grow, similarly to that shown and described with respect to FIG. 1(c). In this and other ways, the redistribution of material from the roller 11200 or from the shaft 11300 may create a precision fit between the roller 11200 and the shaft 11300.

FIGS. 20(a) to 20(f) are partial, cutaway, and other views of another example of portions of a system that may be used in accordance with aspects of the present invention. The portions of the system 12000 of FIGS. 20(a) to 20 (f) differ from system portions 11000 shown in FIGS. 19(a) to 19(f), for example, in that multiple interfering features 12000b are provided on the mating surface 12200a. FIGS. 20(a)-20(c) show portions of system 12000 prior to heat or other treatment (e.g., similar to as shown and described with respect to system 1100 in FIG. 1(b). FIGS. 20(d)-20(f) show the portions of the system 12000 after heat or other treatment (e.g., similar to as shown and described with respect to system 1100 in FIG. 1(b). FIGS. 20(a) and 20(d) are side views of the portions of the system 12000. FIGS. 20(b) and 20(e) are cutaway profile views of the portions of the system 12000. FIGS. 20(c) and 20(f) are close-up views of the areas labeled "F" and "W" in FIGS. 20(b) and 20(e), respectively.

As shown in FIGS. 20(a) to 20(f), the system portions 12000 shown include a shaft 12300, which may comprise metal, and a roller 1220, which may comprise a polymer, for example. System portions 12000 may be used, for example, in joints and/or in devices for remote actuation, such as those used in remote or robotic surgeries.

As shown in FIGS. 20(b), 20(c), 20(e) and 20(f), roller 12200 may have a mating surface 12200a that may include an interfering feature 12200b, similar to interfering feature 1210 shown and described with respect to FIGS. 1(a) to 1(c). In this example, roller 12200 may comprise a material, for example, with a relatively low melting point (e.g., polymer, polymer composite or like material). The roller 12200 may have, for example, a doughnut or annular shape, so as to accommodate the shaft 12300 in the interior or opening of the roller 12200, as shown in the cutaway view in FIG. 20(b). Shaft 12300 may include an interior recess 12300a shown in FIG. 20(b). The shaft 12300 may include a mating surface 12300b for, among other things, mating with the mating surface 12200a and the interfering feature 12200b of the roller 12200.

The shaft 12300 may, for example, be inserted into the roller 12200, as shown in FIG. 20(a). In this example, the mating surface 12300b of the shaft 12300 mates with the mating surface 12200a of the roller 12200, as shown in FIG. 20(b). The resultant configuration is shown in FIG. 20(a).

FIGS. 20(b) 20(c), 20(e) and 20(f) show an interfering feature 12200b included on mating surface 12200a of the roller 12200. The mating surface 12300b of the shaft 12300 may also include one or more interfering features. Such interfering feature or features may function similarly to the interfering feature 1210 shown in FIGS. 1(a) to 1(c).

Inserting the shaft 12300 into the roller 12200 corresponds to one stage of precision fitting shown in FIG. 1(a). In this stage, pressure may be applied to portions of the system, or may be applied to the entire system. Also in this stage, mating surfaces 12300b and 12200a are brought into contact. An interfering feature, such as interfering feature 12200b, may be fashioned so that when mating surfaces 12300b and 12200a are brought into contact, the interfering feature 12200b is compressed (FIGS. 20(b) and 20(c)), as shown for interfering feature 1210 in FIG. 1(a). This contact may create pressure P in the roller 12200 and/or the shaft 12300 in and around the interfering features, similar to that described in conjunction with FIG. 1(b), as further shown in FIGS. 20(b) and 20(c). The pressure P may result in a bowing or distortion D of mating surfaces 12200a (FIGS. 20(b) and 20(c)), as shown for surface 1202 in FIG. 1(a).

In an additional step, heat (or other treatment, e.g., chemical treatment) may be applied to the system 12000 of sufficient temperature and/or degree to partially melt and/or cause flow F of the material in the interfering feature 12200b, as shown for interfering feature 1210 in FIG. 1(b). Such flow F may flow in response to the pressure P of compression of the interfering feature 12200b, for example. The flow F may relieve the pressure P and relieve the bowing or distortion D of mating surfaces 12200a (FIGS. 20(b) and 20(c)), as shown for surface 1202 in FIG. 1(a).

Another stage in the precision fit process may occur after the melting and flow has proceeded for some time period. In this stage, the bowing or distortion D of mating surface 12200a (FIGS. 20(b) and 20(c)), may have been decreased by flow F, for example, as shown for interference feature 1210 in FIG. 1(c). The result is shown in FIGS. 20(e) and 20(f). The adherence of mating surface 12200a to the mating surface 12300b of the shaft may be increased and contact surfaces between the interference features and the mating surfaces may grow, analogously to that shown and described in conjunction with FIG. 1(c). In this and other ways, the redistribution of material from the roller 12200 or from the shaft 12300 may create a precision fit between the roller 12200 and the shaft 12300.

FIGS. 21(a) to 21(d) are perspective views of another example system 13000 that may be used in conjunction with aspects of the present invention. More specifically, FIGS. 21(a) to 21(d) show a system 13000 in which interference features are located on the mating surface of the shaft, instead of the roller. The system 13000 differs from system 11000 shown in FIGS. 19(a) to 19(f), for example in that there are multiple interfering features 12000b on the mating surface 13300a. FIGS. 21(a)-21(b) show the system 13000 prior to heat or other treatment (e.g., as shown for system 1100 in FIG. 1(b). FIGS. 21(c)-21(d) show the system 13000 after heat or other treatment (e.g., as shown for system 1100 in FIG. 1(b). FIGS. 21(a) and 21(c) are side views of the entire system 13000, FIGS. 21(b) and 21(d) are cutaway profile views of the system 13000.

As shown in FIGS. 21(a) to 21(d), the system 13000 includes a shaft 13300, which may be made of polymer, and a roller 13200, which may be made of metal, for example. System 13000 may be used, for example, in joints and/or in devices for remote actuation, such as those used in remote or robotic surgeries.

As shown in FIGS. 21(b) and 21(d), shaft 13300 may have a mating surface 13300a that may include interfering features 13300b, analogous to interfering feature 1210 shown in FIGS. 1(a) to 1(c). In this example, shaft 13300 may include a material, for example, with a relatively low melting point (e.g., polymer, polymer composite or like material). The roller 13200 may have, for example, a doughnut or annular shape so as to accommodate the shaft 13300 in the interior or opening 13201 of the roller 13200, as shown in the cutaway view in FIG. 21(b). The shaft 13300 may include a mating surface 13300a with interfering features 13300b for, among other things, mating with the mating surface 13200a of the roller 13200.

The shaft 13300 may be, for example, inserted into the roller 13200, as shown in FIGS. 21(a) and 21(b). In this example, the mating surface 13300a of the shaft 13300 mates with the mating surface 13200a of the roller 13200, as shown in FIG. 21(b). The resultant configuration is shown in FIG. 21(a).

FIGS. 21(b) and 21(d) show interfering features 13300b included on mating surface 13300a of the shaft 13300. In fact, the mating surface 12300a of the roller 13200 may also include one or more interfering features. In each case, the interfering feature or features would function similarly to as described in conjunction with the interfering feature 1210 shown in FIGS. 1(a) to 1(c).

Inserting the shaft 13300 into the roller 13200 may be similar to one stage of precision fitting shown and described with respect to FIG. 1(a). In this stage, pressure may be applied to only some of the portions of the system, or pressure may be applied to all of the portions of the system shown. In this stage, mating surfaces 13300a and 13200a may be brought into contact. Any interfering feature, such as interfering features 13300b, may be fashioned so that when mating surfaces 13300a and 13200a are brought into contact, the interfering features 13300b become compressed (FIG. 21(b)), as shown for interfering feature 1210 in FIG. 1(a). This contact may create pressure in the shaft 13300 and/or the roller 13200 in and around the interfering features, for example, similar to that shown and described in conjunction with FIG. 1(b), and as further shown in greater detail in FIG. 21(b). The pressure may result in a bowing or distortion of mating surfaces 12200a (FIG. 21(b), similar to as shown and described with respect to surface 1202 in FIG. 1(a).

In another step, heat (or other treatment, e.g., chemical treatment) may be applied to the system 13000 of sufficient temperature and/or degree to partially melt and/or cause flow of the material in the interfering features 13300b, similar to as shown and described with respect to interfering feature 1210 in FIG. 1(b). Such flow may occur, for example, in response to the pressure of compression of the interfering features 13300b. The flow F may relieve the pressure P and relieve the bowing or distortion D of mating surfaces 13200a (see FIG. 21(b), similar to as shown and described with respect to surface 1202 in FIG. 1(a).

Another stage in the precision fit process may occur after the melting and flow has proceeded for some time period. In this stage, the bowing or distortion of mating surface 13300a (FIG. 21(b)), may have been decreased by flow, for example, similar to as shown and described with respect to interference feature 1210 in FIG. 1(c). The result is shown in FIG. 21(d). The adherence of mating surface 13300a to the mating surface 13200a of the roller 13200 may be increased, and contact surfaces between the interference features and the mating surfaces may grow, similar to the process shown and described in conjunction with FIG. 1(c). In this and other ways, the redistribution of material from the roller 13200 or from the shaft 13300 may create a precision fit between the roller 13200 and the shaft 13300.

Figure 23A:
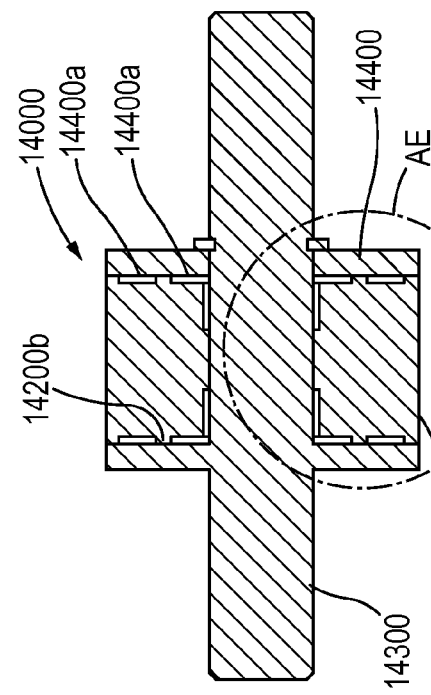
Figure 23B:
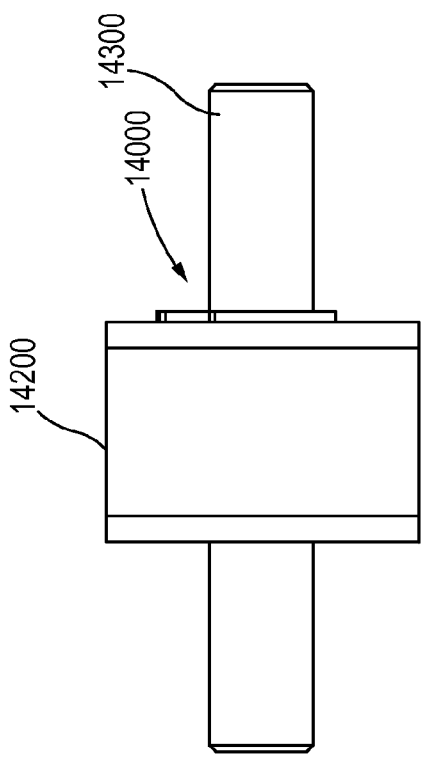
Figure 23D:
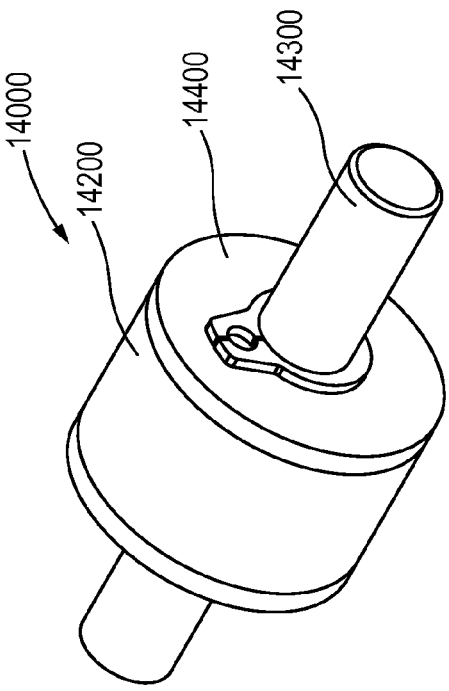
Figure 23C:
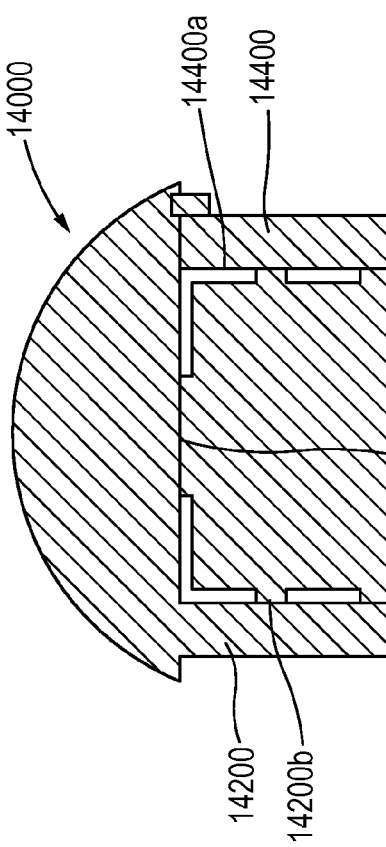

FIGS. 22(a) to 22(d) and 23(a) to 23(d) show various views of another example portion of a system 14000 in accordance with aspects of the present invention. More specifically, FIGS. 22(a) to 22(d) show system portions 14000, in which interference features are located on the mating surface of a roller 14200 for mating with a thrust bearing 14400. FIGS. 22(a)-22(d) show the system portions 14000 prior to heat or other treatment (e.g., similar to as shown and described with respect to system 1100 in FIG. 1(b). FIGS. 23(a)-23(d) show the system portions 14000 after heat or other treatment (e.g., similar to as shown and described with respect to system 1100 in FIG. 1(b). FIGS. 22(a) and 23(a) are side views of the overall system portion 14000. FIGS. 22(b) and 23(b) are cutaway views of the system portion 14000 of FIGS. 22(a) and 23(b), respectively. FIGS. 22(c) and 23(c) are close-up views of areas "AR" and "AE" in FIGS. 22(b) and 23(b), respectively. FIGS. 22(d) and 23(d) are perspective views of the system portion 14000 of FIGS. 22(a) and 23(a), respectively.

As shown in FIGS. 22(a) to 22(d), the system portion 14000 shown includes a shaft 14300, which may comprise metal, and a roller 14200, which may comprise a polymer, for example. System portion 14000 may be used, for example, in joints and/or in devices for remote actuation, such as those used in remote or robotic surgeries.

As shown in FIGS. 22(b), 22(c) and 23(b) and 23(c), roller 14200 may have a mating surface 14200a that may include interfering features 14200b, similar to interfering feature 1210 shown and described with respect to FIGS. 1(a) to 1(c). In the examples of FIGS. 22(a)-(d) and 23(a)-(d), roller 14200 may comprise a material, for example, with a relatively low melting point (e.g., polymer, polymer composite or like material). The roller 14200 may have, for example, a doughnut or annular shape so as to accommodate the shaft 14300 in the interior or opening 14201 of the roller 14200, as shown in the cutaway view in FIG. 22(b). The bearing 14400 may include a mating surface 14400a for, among other things, mating with the mating surface 14200a of the roller 14200.

The shaft 14300 may be, for example, inserted into the roller 14200, as shown in FIGS. 22(b) and 23(b). In these examples, the mating surface 14400a of the bearing 14400 mates with the mating surface 14200a of the roller 14200, as shown in FIGS. 22(b) and 23(b). The resultant configuration is shown in FIGS. 22(a) and 22(d).

FIGS. 22(b) and 23(b) show interfering features 14200b included on mating surface 14200a of the roller 14200. The mating surface 14400a of the bearing 14400 may also include one or more interfering features. In each case, the interfering feature or features may function similarly to the interfering feature 1210 shown and described with respect to FIGS. 1(a) to 1(c).

Inserting the shaft 14300 into the roller 14200 may be similar to one stage of precision fitting shown in FIG. 1(a). In this stage, pressure may be applied to only some or all portions of the system shown in FIGS. 22(a)-(d) and 23(a)-(d). In this stage, mating surfaces 14400a and 14200a are brought into contact. One or more interfering feature, such as interfering features 14200b, may be fashioned so that when mating surfaces 14400a and 14200a are brought into contact, the interfering features 14200b become compressed (see FIGS. 22(b) and 22(c), similarly to as shown and described with respect to interfering feature 1210 in FIG. 1(a). This contact may create pressure in the shaft 14300 and/or the roller 14200 in and around the interfering features. The pressure may result in a bowing or distortion of mating surfaces 14200a (FIGS. 22(b) and 22(c), similarly to as shown and described with respect to surface 1202 in FIG. 1(a).

In another step, heat (or other treatment, e.g., chemical treatment) may be applied to the system 14000 of sufficient temperature and/or degree to partially melt and/or cause flow of the material in the interfering features 14200b. Such flow may occur, for example, in response to the pressure of compression of the interfering features 14200b. The flow may relieve the pressure and relieve the bowing or distortion D of mating surfaces 14200a (FIG. 22(b), similarly to as shown and described with respect to surface 1202 in FIG. 1(a).

Another stage in the precision fit process may occur after the melting and flow has proceeded for some time period. In this stage, the bowing or distortion of mating surface 14200a (FIG. 22(b)), may have been decreased by the flow. The result is shown in FIGS. 23(b) and 23(c). The adherence of mating surface 14400a of the bearing 14400 to the mating surface 14200a of the roller 14200 may be increased, and contact surfaces between the interference features and the mating surfaces may grow due to these operations. In this and other ways, the redistribution of material from the roller 14200 or from the bearing 14400 may create a precision fit between the roller 14200 and the bearing 14400.

Figure 24B:
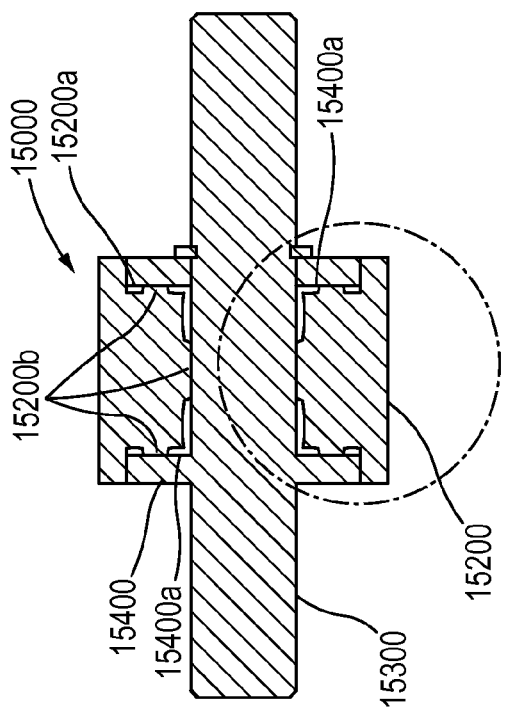
Figure 24D:
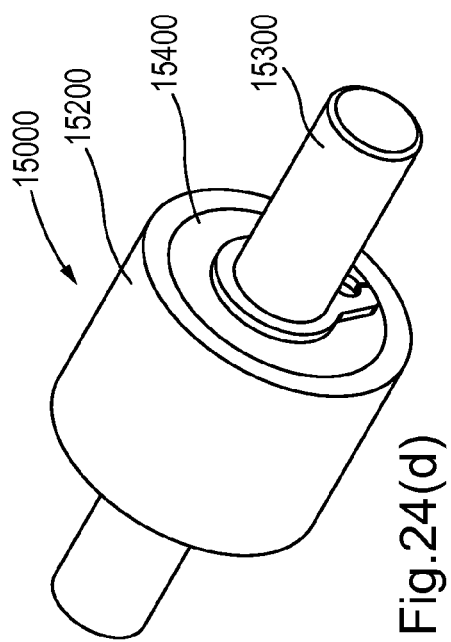
Figure 24A:
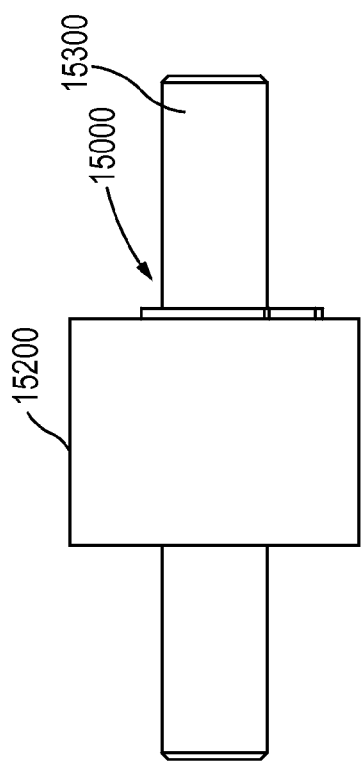
Figure 24C:
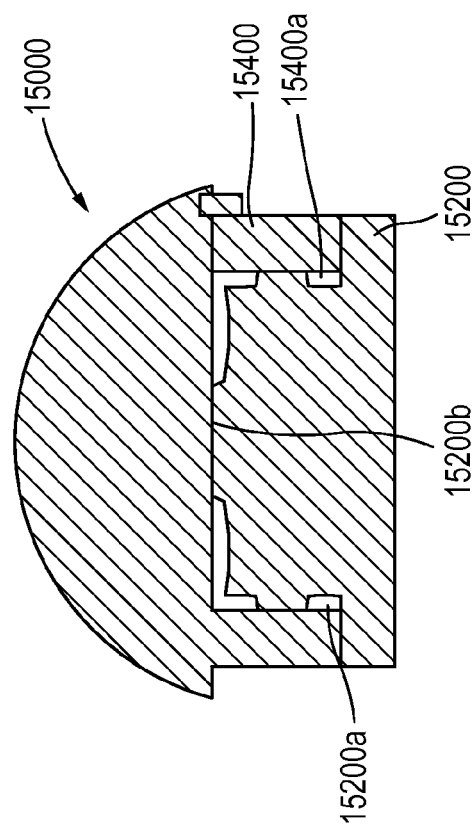

FIGS. 24(a) to 24(d) and 25(a) to 25(d) show various views of another example system portion 15000 in accordance with aspects of the present invention. More specifically, FIGS. 24(a) to 24(d) show a system portion 15000 in which interference features are located on the mating surface of a roller 15200 for mating with a thrust bearing 15400. FIGS. 24(a)-24(d) show the system portion 15000 prior to heat or other treatment (e.g., similarly to as shown and described with respect to system 1100 in FIG. 1(b). FIGS. 25(a)-25(d) show the system 15000 after heat or other treatment (e.g., similarly to as shown and described with respect to system 1100 in FIG. 1(b). FIGS. 24(a) and 25(a) are side views of the entire system portion 15000. FIGS. 24(b) and 25(b) are cutaway views of the system portion 15000 of FIGS. 24(a) and 26(a), respectively. FIGS. 24(c) and 25(c) are close-up views of areas "AR" and "AE" in FIGS. 24(b) and 25(b), respectively. FIGS. 24(d) and 25(d) are perspective side views of the system portion 15000.

As shown in FIGS. 24(a) to 24(d), the system portion 15000 includes a shaft 15300, which may comprise metal, for example, and a roller 15200, which may comprise a polymer, for example. System portion 15000 may be used, for example, in joints and/or in devices for remote actuation, such as those used in remote or robotic surgeries.

As shown in FIGS. 24(b), 24(c), 25(b) and 25(c), roller 15200 may have a mating surface 15200a that may include interfering features 15200b, similar to the interfering feature 1210 shown and described with respect to FIGS. 1(a) to 1(c). In this example, roller 15200 may include a material, for example, with a relatively low melting point (e.g., polymer, polymer composite or like material). The roller 15200 may have, for example, a doughnut or annular shape so as to accommodate the shaft 15300 in the interior or opening of the roller 15200, as shown in the cutaway view in FIG. 24(b). The bearing 15400 may include a mating surface 15400a for, among other things, mating with the mating surface 15200a of the roller 15200.

The shaft 15300 may, for example, be inserted into the roller 15200, as shown in FIGS. 24(b) and 25(b). In this example, the mating surface 15400a of the bearing 15400 mates with the mating surface 15200a of the roller 15200, as shown in FIG. 24(b). The resultant configuration is shown in FIGS. 24(a) and 24(d).

FIGS. 24(b) and 25(b) show interfering features 15200b included on mating surface 15200a of the roller 15200. The mating surface 15400a of the bearing 15400 may also include one or more interfering features. In each case, the interfering feature or features may function similarly to the interfering feature 1210 shown and described with respect to FIGS. 1(a) to 1(c).

Inserting the shaft 15300 into the roller 15200 may be similar to the stage of precision fitting shown and described with respect to FIG. 1(a). In this stage, pressure may be applied to some or all portions of the system shown. In this stage, mating surfaces 15400a and 15200a may be brought into contact. An interfering feature, such as interfering features 15200b, may be fashioned so that when mating surfaces 15400a and 15200a are brought into contact, the interfering features 15200b become compressed (FIGS. 24(b) and 24(c)). This contact may create pressure in the shaft 15300 and/or the roller 15200 in and around the interfering features, similar to that shown in FIG. 1(b), as shown in FIG. 21(b). The pressure may result in a bowing or distortion of mating surfaces 12400a (FIGS. 24(b) and 24(c)), similar to as shown and described with respect to surface 1202 in FIG. 1(a).

In another step, heat (or other treatment, e.g., chemical treatment) may be applied to the system 15000 of sufficient temperature and/or degree to partially melt and/or cause flow of the material in the interfering features 15200b, similarly to as shown and described with respect to interfering feature 1210 in FIG. 1(b). Such flow may occur, for example, in response to the pressure of compression of the interfering features 15200b. The flow may relieve the pressure and relieve the bowing or distortion of mating surfaces 15200a (FIG. 24(b)).

Another stage in the precision fit process may occur after the melting and flow has proceeded for some time period. In this stage, the bowing or distortion of mating surface 15200a (FIG. 24(b)), may have been decreased by the flow, similarly to as shown and described with respect to the interference feature 1210 in FIG. 1(c). The result is shown in FIGS. 25(b) and 25(c). The adherence of mating surface 15400a of the bearing 15400 to the mating surface 15200a of the roller 15200 may be increased, and contact surfaces between the interference features and the mating surfaces may grow, similarly to as shown and described with respect to FIG. 1(c). In this and other ways, the redistribution of material from the roller 15200 or from the bearing 15400 may create a precision fit between the roller 15200 and the bearing 15400.

Figure 26B:
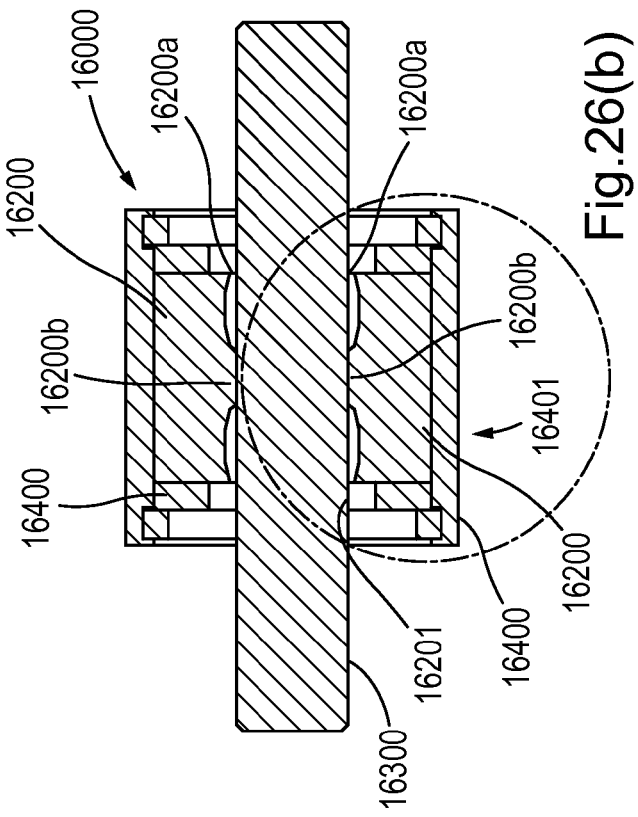
FIGS. 26(a) to 27(d) show various views of another example of system portions in accordance with aspects of the present invention.
Figure 26D:
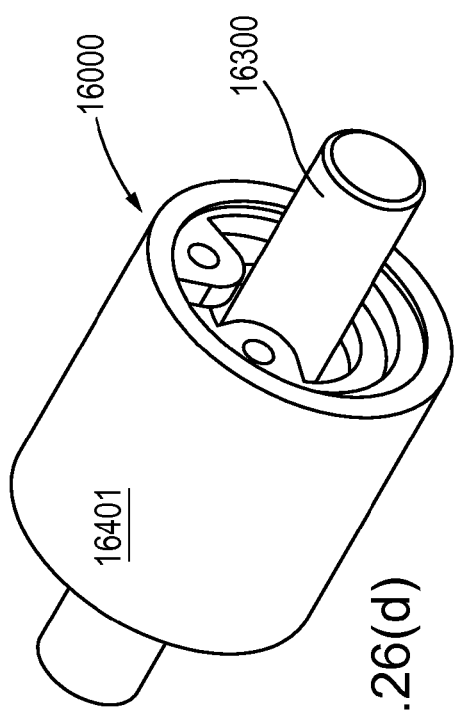
Figure 26A:
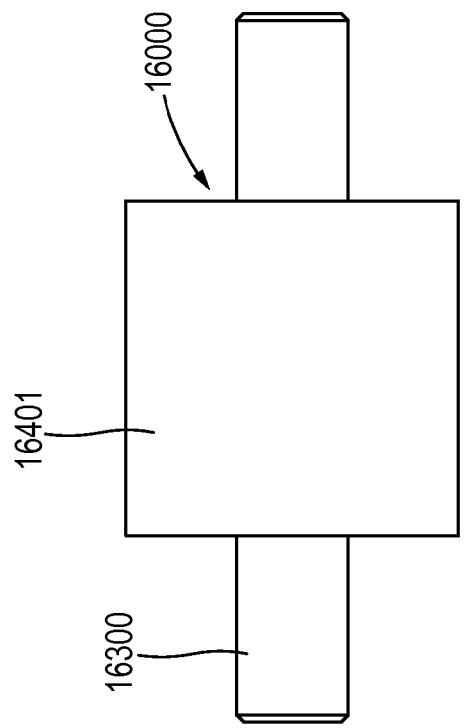
Figure 26C:
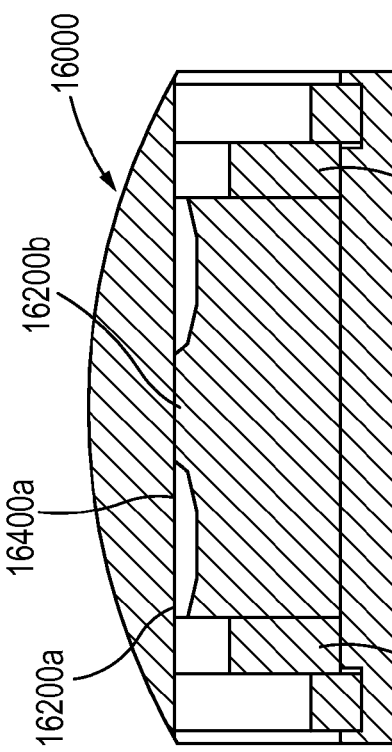
Figure 27B:
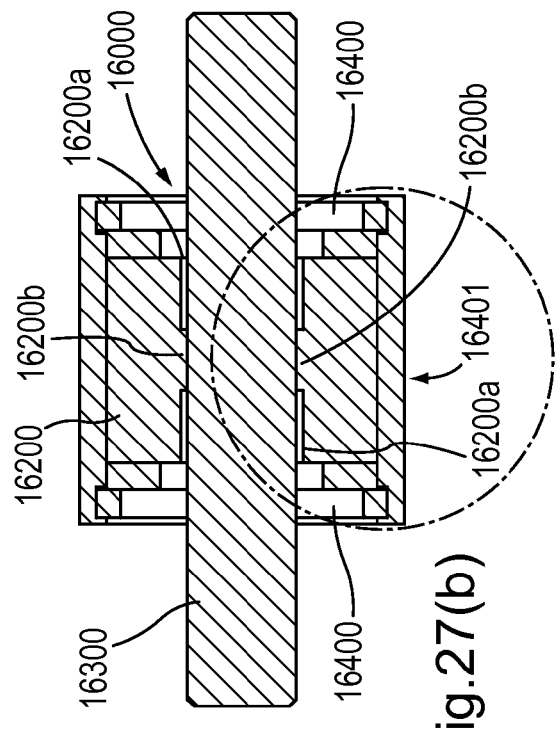
Figure 27D:
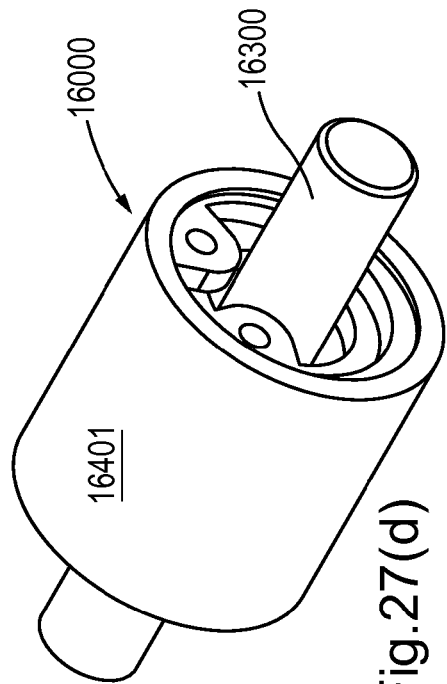
Figure 27A:
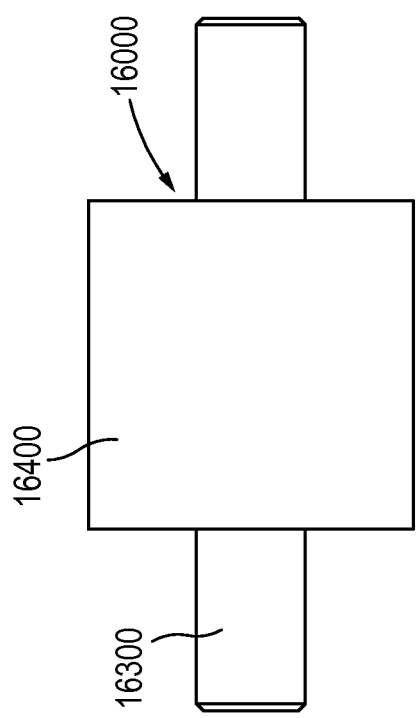
Figure 27C:
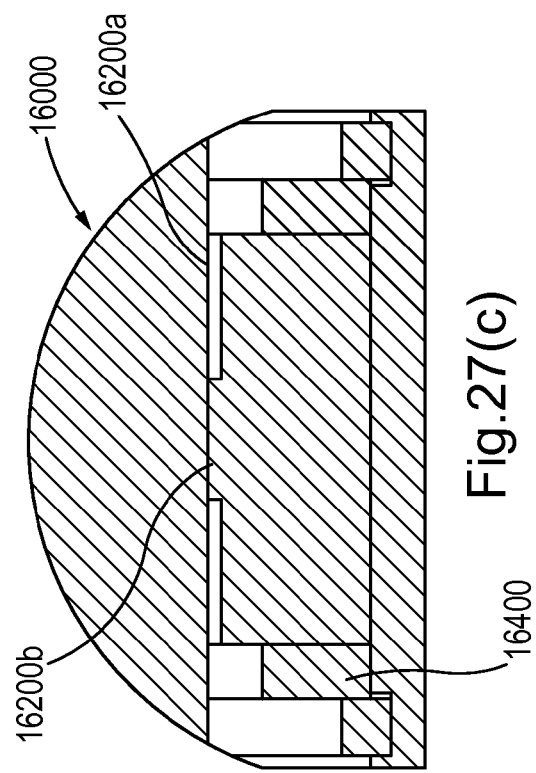

FIGS. 26(a) to 26(d) and 27(a) to 27(d) show various views of another example system portion 16000 in accordance with aspects of the present invention. More specifically, FIGS. 26(a) to 26(d) show a system portion 16000 in which interference features are located on the mating surface of a roller 16200 for mating with the housing 16400 of a captured bearing 16401. FIGS. 26(a)-26(d) show the system portion 16000 prior to heat or other treatment. FIGS. 27(a)-27(d) show the system portion 16000 after heat or other treatment. FIGS. 26(a) and 27(a) are side views of the system portion 16000. FIGS. 26(b) and 27(b) are cutaway views of the system portion 16000. FIGS. 26(c) and 27(c) are close-up views of areas "AN" and "AJ" in FIGS. 26(b) and 27(b), respectively. FIGS. 26(d) and 27(d) are perspective views of the system portion 16000.

As shown in FIGS. 26(a) to 26(d), the system portion 16000 includes a shaft 16300, which may comprise metal, and a roller 16200, which may comprise a polymer, for example. System portion 16000 may be used, for example, in joints and/or in devices for remote actuation, such as those used in remote or robotic surgeries. The system portion 16000 shown in Figures further includes a bearing 16001 that has a housing 16400.

As shown in FIGS. 26(b), 26(c), 27(b) and 27(c), roller 16200 may have a mating surface 16200a, which may include interfering features 16200b. In this example, roller 16200 may include a material, for example, with a relatively low melting point (e.g., polymer, polymer composite or like material). The roller 16200 may have, for example, a doughnut or annular shape so as to accommodate the shaft 16300 in the interior or opening of the roller 16200, as shown in the cutaway view in FIG. 26(b). The housing 16400 of the bearing 16401 may include a mating surface 16400a for, among other things, mating with the mating surface 16200a of the roller 16200.

The shaft 16300 may, for example, be inserted into the roller 16200, as shown in FIGS. 26(b) and 27(b). In this example, the mating surface 16400a of the housing 16400 of the bearing 16401 mates with the mating surface 16200*a* of the roller 16200, as shown in FIG. 26(*b*). The resultant configuration is shown in FIGS. 26(*a*) and 26(*d*).

FIGS. 26(*b*) and 27(*b*) show interfering features 16200*b* included on mating surface 16200*a* of the roller 16200. The mating surface 16400*a* of the housing 16400 of the bearing 16401 may also include one or more interfering features. In each case, the interfering feature or features may function similarly as the interfering feature 1210 shown in FIGS. 1(*a*) to 1(*c*).

Inserting the shaft 16300 into the roller 16200 corresponds to the stage of precision fitting shown in FIG. 1(*a*). In this stage, pressure may be applied to portions of the system, or may be applied to the entire system. In this stage, mating surfaces 16400*a* and 16200*a* may be brought into contact. An interfering feature, such as interfering features 16200*b*, may be fashioned so that when mating surfaces 16400*a* and 16200*a* are brought into contact, the interfering features 16200*b* become compressed (FIGS. 26(*b*) and 26(*c*)), as shown for interfering feature 1210 in FIG. 1(*a*). This contact may create pressure P in the shaft 16300 and/or the roller 16200 in and around the interfering features, similar to that shown in FIG. 1(*b*), as shown in FIG. 21(*b*). The pressure P may result in a bowing or distortion D of mating surfaces 12600*a* (FIGS. 26(*b*) and 26(*c*)), as shown for surface 1202 in FIG. 1(*a*).

In another step, heat (or other treatment, e.g., chemical treatment) may be applied to the system 16000 of sufficient temperature and/or degree to partially melt and/or cause flow F of the material in the interfering features 16200*b*, as shown for interfering feature 1210 in FIG. 1(*b*). Such flow F may occur, for example, in response to the pressure P of compression of the interfering features 16200*b*. The flow F may relieve the pressure P and relieve the bowing or distortion D of mating surfaces 16200*a* (FIG. 26(*b*)), as shown for surface 1202 in FIG. 1(*a*).

Another stage in the precision fit may occur after the melting and flow has proceeded for some time period. In this stage, the bowing or distortion D of mating surface 16200*a* (FIG. 26(*b*)), may have been decreased by flow F, as shown for interference feature 1210 in FIG. 1(*c*). The result is shown in FIGS. 27(*b*) and 27(*c*). The adherence of mating surface 16400*a* of the housing 16400 of the bearing 16401 to the mating surface 16200*a* of the roller 16200 may be increased, and contact surfaces between the interference features and the mating surfaces may grow, analogously to that shown in FIG. 1(*c*). In this and other ways, the redistribution of material from the roller 16200 or from the housing 16400 of the bearing 16401 may create a precision fit between the roller 16200 and the bearing 16400.

FIGS. 28(*a*) to 28(*c*) show various view of another example system portion 17000 in accordance with aspects of the present invention. More specifically, FIGS. 28(*a*) to 28(*c*) show a system portion 17000 in which interference features are located on the mating surface of a screw nut 17200 for mating with a screw 17300. Similarly to as shown and discussed with regard to the system portions 10000-16000, interfering features may be incorporated onto the mating surface 17200*a* of the screw nut 17200 (FIG. 28(*c*)). Applying a heating and/or other treatment, similarly to as described and shown above in the context of system portions 10000-16000, may create the precision fit shown in FIG. 28(*c*) between the mating surface 17200*a* of the screw nut and a mating surface 17300*a* of a screw 17300. Such features may be used, for example, to improve the functioning of the screw system portion 17000 by decreasing asperities in the mating surfaces 17300*a* and 17200*a*. This may, among other things, improve the functioning of the screw system 17000.

Although aspects of the invention have been described with reference to various features and examples with respect to a surgical instrument, it is within the scope and spirit hereof to incorporate or use such aspects with any suitable mechanical device. Further, while some features have been described with reference to a surgeon, aspects of the invention may be used with another user, depending on circumstances in which used. Thus, it should be understood that numerous and various modifications may be made without departing from the spirit hereof.

The invention claimed is:

1. A method of creating a precision-fit joint, comprising:
creating a mating surface on a first joint component so that the mating surface includes one or more interfering features;
connecting a second joint component with the mating surface such that the one or more interfering features are compressed, wherein the first joint component is a link for a chain comprising a plurality of links and the second joint component is a pin that connects the first joint component with another link in the chain;
treating the mating surface so as to induce flow of material from the one or more interfering features to an area between the first joint component and the second joint component; and
applying a stabilization mechanism that dampens vibrations between the first and second joint components, wherein the stabilizing mechanism stabilizes operation of a hydraulically controlled surgical device.

2. The method of claim 1, wherein treating the mating surface includes heating the mating surface above a glass transition temperature or melting temperature of the mating surface.

3. The method of claim 1, wherein treating the mating surface includes chemically modifying the mating surface.

4. The method of claim 1 wherein creating the interfering feature further comprises:
defining a pattern that allows ventilation during the flow of the material to prevent formation of a bubble.

5. The method of claim 4 wherein the pattern comprises a screw thread pattern.

6. The method of claim 1, further comprising:
forming the interfering feature from a polymeric material.

7. The method of claim 1, further comprising:
applying external pressure to the first joint component.

* * * * *